(12) United States Patent
Belmonte Martnez et al.

(10) Patent No.: US 9,095,609 B2
(45) Date of Patent: Aug. 4, 2015

(54) OPHTHALMIC COMPOSITION COMPRISING WS-12 AND METHODS TO TREAT XEROPHTHALMIA

(75) Inventors: Carlos Belmonte Martnez, San Joan d'Alacant (ES); Juana Gallar Martinez, San Joan d'Alacant (ES); Antonio Ferrer Montiel, San Joan d'Alacant (ES); Asia Fernández Carvajal, San Joan d'Alacant (ES); Félix Viana De La Iglesia, San Joan d'Alacant (ES)

(73) Assignees: UNIVERSIDAD MIGUEL HERNÁNDEZ DE ELCHE (ES); CONSEJO SUPERIOR DE INVESTIGACIONES CIENTÍFICAS (C.S.I.C.) (ES)

( * ) Notice: Subject to any disclaimer, the term of this patent is extended or adjusted under 35 U.S.C. 154(b) by 0 days.

(21) Appl. No.: 13/821,840

(22) PCT Filed: Sep. 8, 2011

(86) PCT No.: PCT/ES2011/070627
§ 371 (c)(1),
(2), (4) Date: May 29, 2013

(87) PCT Pub. No.: WO2012/032209
PCT Pub. Date: Mar. 15, 2012

(65) Prior Publication Data
US 2013/0245231 A1    Sep. 19, 2013

(30) Foreign Application Priority Data
Sep. 8, 2010   (ES) .................................... 201031341

(51) Int. Cl.
| | |
|---|---|
| A01N 31/08 | (2006.01) |
| A61K 31/05 | (2006.01) |
| A01N 33/18 | (2006.01) |
| A01N 33/24 | (2006.01) |
| A61K 31/04 | (2006.01) |
| A01N 27/00 | (2006.01) |
| A61K 31/015 | (2006.01) |
| A61K 45/00 | (2006.01) |
| A61K 31/00 | (2006.01) |
| A61K 31/045 | (2006.01) |
| A61K 31/047 | (2006.01) |
| A61K 31/075 | (2006.01) |
| A61K 31/16 | (2006.01) |
| A61K 31/164 | (2006.01) |
| A61K 31/167 | (2006.01) |
| A61K 31/17 | (2006.01) |
| A61K 31/196 | (2006.01) |
| A61K 31/215 | (2006.01) |
| A61K 31/22 | (2006.01) |
| A61K 31/221 | (2006.01) |
| A61K 31/245 | (2006.01) |
| A61K 31/27 | (2006.01) |
| A61K 31/352 | (2006.01) |
| A61K 31/357 | (2006.01) |
| A61K 31/381 | (2006.01) |
| A61K 31/4025 | (2006.01) |
| A61K 31/4164 | (2006.01) |
| A61K 31/4745 | (2006.01) |
| A61K 31/496 | (2006.01) |
| A61K 31/505 | (2006.01) |
| A61K 31/55 | (2006.01) |

(Continued)

(52) U.S. Cl.
CPC ................. *A61K 45/00* (2013.01); *A61K 31/00* (2013.01); *A61K 31/045* (2013.01); *A61K 31/047* (2013.01); *A61K 31/075* (2013.01); *A61K 31/16* (2013.01); *A61K 31/164* (2013.01); *A61K 31/167* (2013.01); *A61K 31/17* (2013.01); *A61K 31/196* (2013.01); *A61K 31/215* (2013.01); *A61K 31/22* (2013.01); *A61K 31/221* (2013.01); *A61K 31/245* (2013.01); *A61K 31/27* (2013.01); *A61K 31/352* (2013.01); *A61K 31/357* (2013.01); *A61K 31/381* (2013.01); *A61K 31/4025* (2013.01); *A61K 31/4164* (2013.01); *A61K 31/4745* (2013.01); *A61K 31/496* (2013.01); *A61K 31/505* (2013.01); *A61K 31/55* (2013.01); *A61K 31/662* (2013.01); *A61K 31/713* (2013.01); *A61K 31/7105* (2013.01)

(58) Field of Classification Search
None
See application file for complete search history.

(56) References Cited

U.S. PATENT DOCUMENTS

| 7,893,110 B2 * | 2/2011 | Galopin et al. ................ 514/613 |
| 2003/0008805 A1 * | 1/2003 | Honma et al. .................... 514/1 |

(Continued)

FOREIGN PATENT DOCUMENTS

| WO | 03099278 A1 | 12/2003 |
| WO | 2007017092 A1 | 2/2007 |

(Continued)

OTHER PUBLICATIONS

International Search Report, Mar. 21, 2012.

(Continued)

*Primary Examiner* — Robert Landsman
(74) *Attorney, Agent, or Firm* — Sterne, Kessler, Goldstein & Fox P.L.L.C.

(57) ABSTRACT

The invention relates to therapeutic compositions for the treatment of dry eye, more specifically to compositions comprising a TRPM8 receptor agonist ligand. Furthermore, the invention relates to therapeutic compositions for the treatment of epiphora, more specifically to compositions comprising a TRPM8 receptor antagonist.

24 Claims, 9 Drawing Sheets

(51) Int. Cl.
*A61K 31/662* (2006.01)
*A61K 31/7105* (2006.01)
*A61K 31/713* (2006.01)

(56) References Cited

U.S. PATENT DOCUMENTS

| | | | |
|---|---|---|---|
| 2005/0090514 A1* | 4/2005 | Reynolds et al. | 514/269 |
| 2007/0010574 A1* | 1/2007 | Plath et al. | 514/422 |
| 2008/0214654 A1 | 9/2008 | Lampe et al. | |
| 2009/0269369 A1* | 10/2009 | Doi et al. | 424/195.18 |
| 2011/0053137 A1* | 3/2011 | Julius et al. | 435/4 |
| 2011/0223222 A1* | 9/2011 | Spyros Botsaris et al. | 424/401 |

FOREIGN PATENT DOCUMENTS

| | | |
|---|---|---|
| WO | 2007099503 A2 | 9/2007 |
| WO | 2010017609 A2 | 2/2010 |
| WO | 2010021882 A2 | 2/2010 |

OTHER PUBLICATIONS

Haghighi, Afshin Borhani, et al.; "Therapeutic potentials of menthol in migraine headache: Possible mechanisms of action," Med Hypotheses, 2007, p. 455, vol. 69.

Parra, Andrés, et al.; "Ocular surface wetness is regulated by TRPM8-dependent cold thermoreceptors of cornea," Nature Medicine, 2010, pp. 1369-1399, vol. 16.

Moss, Scot E., et al.; "Long-term Incidence of Dry Eye in an Older Population," Optometry and Vision Science, 2008, pp. 668-674, vol. 85.

Barker, Ke, et al.; "Burning mouth syndrome: an update on recent findings," Australian Dental Journal, 2005, pp. 220-223, vol. 50.

Leiblum, Sandra R., et al.; "Vaginal Dryness: A Comparison of Prevalence and Interventions in 11 countries," Journal of Sexual Medicine, 2009, pp. 2425-2433, vol. 6.

Dartt, Darlene A.; "Neural Regulation of Lacrimal Gland Secretory Processes: Relevance in Dry Eye Diseases," Prog Retin Eye Res., 2009, pp. 155-177, vol. 28.

Acosta, M. Carmen, et al.; "Tear Secretion Induced by Selective Stimulation of Corneal and Conjunctival Sensory Nerve Fibers," Investigative Ophthalmology & Visual Science, 2004, pp. 2333-2336, vol. 45.

Belmonte, Carlos, et al.; "Neural basis of sensation in intact and injured corneas," Experimental Eye Research, 2004, pp. 513-525, vol. 78.

Hirata, H. et al., "Cold-Sensitive Corneal Afferents Respond to a Variety of Ocular Stimuli Central to Tear Production: Implications for Dye Eye Disease," Investigative Ophthalmology & Visual Science, vol. 51, 3969-3976 (2010), Cadmus (United States).

* cited by examiner

SEQUENCE LISTING

<160> NUMBER OF SEQ ID NOS: 9

<210> SEQ ID NO 1
<211> LENGTH: 1104
<212> TYPE: PRT
<213> ORGANISM: Homo sapiens

<400> SEQUENCE: 1

Met Ser Phe Arg Ala Ala Arg Leu Ser Met Arg Asn Arg Arg Asn Asp
1               5                   10                  15

Thr Leu Asp Ser Thr Arg Thr Leu Tyr Ser Ser Ala Ser Arg Ser Thr
            20                  25                  30

-continued

```
Asp Leu Ser Tyr Ser Glu Ser Asp Leu Val Asn Phe Ile Gln Ala Asn
         35                  40                  45

Phe Lys Lys Arg Glu Cys Val Phe Phe Thr Lys Asp Ser Lys Ala Thr
 50                  55                  60

Glu Asn Val Cys Lys Cys Gly Tyr Ala Gln Ser Gln His Met Glu Gly
 65                  70                  75                  80

Thr Gln Ile Asn Gln Ser Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Ser Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Ala Glu Gly Tyr Phe Leu Ala Gln Tyr
225                 230                 235                 240

Leu Met Asp Asp Phe Thr Arg Asp Pro Leu Tyr Ile Leu Asp Asn Asn
                245                 250                 255

His Thr His Leu Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ile Gln Asp Ser Asn Tyr Gly Gly Lys Ile Pro Ile Val Cys Phe
    290                 295                 300

Ala Gln Gly Gly Gly Lys Glu Thr Leu Lys Ala Ile Asn Thr Ser Ile
305                 310                 315                 320

Lys Asn Lys Ile Pro Cys Val Val Val Glu Gly Ser Gly Gln Ile Ala
                325                 330                 335

Asp Val Ile Ala Ser Leu Val Glu Val Glu Asp Ala Leu Thr Ser Ser
            340                 345                 350

Ala Val Lys Glu Lys Leu Val Arg Phe Leu Pro Arg Thr Val Ser Arg
        355                 360                 365

Leu Pro Glu Glu Glu Thr Glu Ser Trp Ile Lys Trp Leu Lys Glu Ile
    370                 375                 380

Leu Glu Cys Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Ser Glu Gln Asp Lys Asp Asn Trp Asn Gly Gln Leu Lys Leu
            420                 425                 430

Leu Leu Glu Trp Asn Gln Leu Asp Leu Ala Asn Asp Glu Ile Phe Thr
        435                 440                 445

Asn Asp Arg Arg Trp Glu Ser Ala Asp Leu Gln Glu Val Met Phe Thr
```

```
                    450                 455                 460
Ala Leu Ile Lys Asp Arg Pro Lys Phe Val Arg Leu Phe Leu Glu Asn
465                 470                 475                 480

Gly Leu Asn Leu Arg Lys Phe Leu Thr His Asp Val Leu Thr Glu Leu
                    485                 490                 495

Phe Ser Asn His Phe Ser Thr Leu Val Tyr Arg Asn Leu Gln Ile Ala
                500                 505                 510

Lys Asn Ser Tyr Asn Asp Ala Leu Leu Thr Phe Val Trp Lys Leu Val
            515                 520                 525

Ala Asn Phe Arg Arg Gly Phe Arg Lys Glu Asp Arg Asn Gly Arg Asp
        530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                    565                 570                 575

Ser Lys Val Ile Trp Glu Gln Thr Arg Gly Cys Thr Leu Ala Ala Leu
                580                 585                 590

Gly Ala Ser Lys Leu Leu Lys Thr Leu Ala Lys Val Lys Asn Asp Ile
            595                 600                 605

Asn Ala Ala Gly Glu Ser Glu Leu Ala Asn Glu Tyr Glu Thr Arg
        610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                    645                 650                 655

Leu Glu Leu Ala Val Glu Ala Thr Asp Gln His Phe Ile Ala Gln Pro
                660                 665                 670

Gly Val Gln Asn Phe Leu Ser Lys Gln Trp Tyr Gly Glu Ile Ser Arg
            675                 680                 685

Asp Thr Lys Asn Trp Lys Ile Ile Leu Cys Leu Phe Ile Ile Pro Leu
        690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                    725                 730                 735

Val Phe Ser Trp Asn Val Phe Tyr Ile Ala Phe Leu Leu Leu Phe
                740                 745                 750

Ala Tyr Val Leu Leu Met Asp Phe His Ser Val Pro His Pro Pro Glu
            755                 760                 765

Leu Val Leu Tyr Ser Leu Val Phe Val Leu Phe Cys Asp Glu Val Arg
        770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                    805                 810                 815

Leu His Ser Ser Asn Lys Ser Ser Leu Tyr Ser Gly Arg Val Ile Phe
                820                 825                 830

Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
        850                 855                 860

Ile Asp Val Phe Phe Phe Leu Phe Leu Phe Ala Val Trp Met Val Ala
865                 870                 875                 880
```

```
Phe Gly Val Ala Arg Gln Gly Ile Leu Arg Gln Asn Glu Gln Arg Trp
                885                 890                 895
Arg Trp Ile Phe Arg Ser Val Ile Tyr Glu Pro Tyr Leu Ala Met Phe
        900                 905                 910
Gly Gln Val Pro Ser Asp Val Asp Gly Thr Thr Tyr Asp Phe Ala His
            915                 920                 925
Cys Thr Phe Thr Gly Asn Glu Ser Lys Pro Leu Cys Val Glu Leu Asp
    930                 935                 940
Glu His Asn Leu Pro Arg Phe Pro Glu Trp Ile Thr Ile Pro Leu Val
945                 950                 955                 960
Cys Ile Tyr Met Leu Ser Thr Asn Ile Leu Leu Val Asn Leu Leu Val
                965                 970                 975
Ala Met Phe Gly Tyr Thr Val Gly Thr Val Gln Glu Asn Asn Asp Gln
            980                 985                 990
Val Trp Lys Phe Gln Arg Tyr Phe Leu Val Gln Glu Tyr Cys Ser Arg
        995                 1000                1005
Leu Asn Ile Pro Phe Pro Phe Ile Val Phe Ala Tyr Phe Tyr Met
    1010                1015                1020
Val Val Lys Lys Cys Phe Lys Cys Cys Cys Lys Glu Lys Asn Met
    1025                1030                1035
Glu Ser Ser Val Cys Cys Phe Lys Asn Glu Asp Asn Glu Thr Leu
    1040                1045                1050
Ala Trp Glu Gly Val Met Lys Glu Asn Tyr Leu Val Lys Ile Asn
    1055                1060                1065
Thr Lys Ala Asn Asp Thr Ser Glu Glu Met Arg His Arg Phe Arg
    1070                1075                1080
Gln Leu Asp Thr Lys Leu Asn Asp Leu Lys Gly Leu Leu Lys Glu
    1085                1090                1095
Ile Ala Asn Lys Ile Lys
    1100

<210> SEQ ID NO 2
<211> LENGTH: 5621
<212> TYPE: DNA
<213> ORGANISM: Homo sapiens

<400> SEQUENCE: 2
aagaaaatcc tgcttgacaa aaaccgtcac ttaggaaaag atgtcctttc gggcagccag    60
gctcagcatg aggaacagaa ggaatgacac tctggacagc acccggaccc tgtactccag   120
cgcgtctcgg agcacagact tgtcttacag tgaaagcgac ttggtgaatt ttattcaagc   180
aaattttaag aaacgagaat gtgtcttctt taccaaagat tccaaggcca cggagaatgt   240
gtgcaagtgt ggctatgccc agagccagca catggaaggc acccagatca accaaagtga   300
gaaatggaac tacaagaaac acaccaagga atttcctacc gacgcctttg gggatattca   360
gtttgagaca ctggggaaga aagggaagta tatacgtctg tcctgcgaca cggacgcgga   420
aatcctttac gagctgctga cccagcactg gcacctgaaa acacccaacc tggtcatttc   480
tgtgaccggg gccgccaaga cttcgcccct gaagccgcgc atgcgcaaga tcttcagccg   540
gctcatctac atcgcgcagt ccaaaggtgc ttggattctc acgggaggca cccattatgg   600
cctgatgaag tacatcgggg aggtggtgag agataacacc atcagcagga gttcagagga   660
gaatattgtg gccattggca tagcagcttg gggcatggtc tccaaccggg acaccctcat   720
caggaattgc gatgctgagg gctattttt agcccagtac cttatggatg acttcacaag   780
```

```
agatccactg tatatcctgg acaacaacca cacacatttg ctgctcgtgg acaatggctg    840
tcatggacat cccactgtcg aagcaaagct ccggaatcag ctagagaagt atatctctga    900
gcgcactatt caagattcca actatggtgg caagatcccc attgtgtgtt ttgcccaagg    960
aggtggaaaa gagactttga aagccatcaa tacctccatc aaaaataaaa ttccttgtgt   1020
ggtggtggaa ggctcgggcc agatcgctga tgtgatcgct agcctggtgg aggtggagga   1080
tgccctgaca tcttctgccg tcaaggagaa gctggtgcgc tttttacccc gcacggtgtc   1140
ccggctgcct gaggaggaga ctgagagttg atcaaatgg ctcaaagaaa ttctcgaatg    1200
ttctcaccta ttaacagtta ttaaaatgga agaagctggg gatgaaattg tgagcaatgc   1260
catctcctac gctctataca aagccttcag caccagtgag caagacaagg ataactggaa   1320
tgggcagctg aagcttctgc tggagtggaa ccagctggac ttagccaatg atgagatttt   1380
caccaatgac cgccgatggg agtctgctga ccttcaagaa gtcatgttta cggctctcat   1440
aaaggacaga cccaagtttg tccgcctctt tctggagaat ggcttgaacc tacgaagtt    1500 tctcacccat gatgtcctca ctgaactctt ctccaaccac ttcagcacgc ttgtgtaccg   1560
gaatctgcag atcgccaaga attcctataa tgatgccctc ctcacgtttg tctggaaact   1620
ggttgcgaac ttccgaagag gcttccggaa ggaagacaga aatggccggg acgagatgga   1680
catagaactc cacgacgtgt ctcctattac tcggcacccc ctgcaagctc tcttcatctg   1740
ggccattctt cagaataaga aggaactctc caaagtcatt tgggagcaga ccaggggctg   1800
cactctggca gccctgggag ccagcaagct tctgaagact ctggccaaag tgaagaacga   1860
catcaatgct gctggggagt ccgaggagct ggctaatgag tacgagaccc gggctgttga   1920
gctgttcact gagtgttaca gcagcgatga agacttggca gaacagctgc tggtctattc   1980
ctgtgaagct tggggtggaa gcaactgtct ggagctggcg gtggaggcca cagaccagca   2040
tttcatcgcc cagcctgggg tccagaattt tcttctaag caatggtatg agagagatttc   2100 ccgagacacc aagaactgga agattatcct gtgtctgttt attataccct tggtgggctg   2160
tggctttgta tcatttagga agaaacctgt cgacaagcac aagaagctgc tttggtacta   2220
tgtggcgttc ttcacctccc ccttcgtggt cttctcctgg aatgtggtct tctacatcgc   2280
cttcctcctg ctgtttgcct acgtgctgct catggatttc cattcggtgc cacacccccc   2340
cgagctggtc ctgtactcgc tggtcttttgt cctcttctgt gatgaagtga cagtggta    2400 cgtaaatggg gtgaattatt ttactgacct gtggaatgtg atggacacgc tggggctttt   2460
ttacttcata gcaggaattg tatttcggct ccactcttct aataaaagct ctttgtattc   2520
tggacgagtc attttctgtc tggactacat tattttcact ctaagattga tccacatttt   2580
tactgtaagc agaaacttag gacccaagat tataatgctg cagaggatgc tgatcgatgt   2640
gttcttcttc ctgttcctct ttgcggtgtg gatggtggcc tttggcgtgg ccaggcaagg   2700
gatccttagg cagaatgagc agcgctgag gtggatattc cgttcggtca tctacgagcc   2760
ctacctggcc atgttcggcc aggtgcccag tgacgtggat ggtaccacgt atgactttgc   2820
ccactgcacc ttcactggga atgagtccaa gccactgtgt gtggagctgg atgagcacaa   2880
cctgccccgg ttccccgagt ggatcaccat ccccctggtt gcatctacca tgttatccac   2940
caacatcctg ctggtcaacc tgctggtcgc catgtttggc tacacggtgg caccgtcca    3000 ggagaacaat gaccaggtct ggaagttcca gaggtacttc ctggtgcagg agtactgcag   3060
ccgcctcaat atcccttcc ccttcatcgt cttcgcttac ttctacatgg tggtgaagaa   3120
```

```
gtgcttcaag tgttgctgca aggagaaaaa catggagtct tctgtctgct gtttcaaaaa    3180
tgaagacaat gagactctgg catgggaggg tgtcatgaag gaaaactacc ttgtcaagat    3240
caacacaaaa gccaacgaca cctcagagga aatgaggcat cgatttagac aactggatac    3300
aaagcttaat gatctcaagg gtcttctgaa agagattgct aataaaatca ataaaactg    3360 tatgaactct aatggagaaa aatctaatta tagcaagatc atattaagga atgctgatga    3420
acaattttgc tatcgactac taaatgagag attttcagac ccctgggtac atggtggatg    3480
attttaaatc accctagtgt gctgagacct tgagaataaa gtgtgtgatt ggtttcatac    3540
ttgaagacgg atataaagga agaatatttc ctttatgtgt ttctccagaa tggtgcctgt    3600
ttctctctgt gtctcaatgc ctgggactgg aggttgatag tttaagtgtg ttcttaccgc    3660
ctcctttttc ctttaatctt atttttgatg aacacatata taggagaaca tctatcctat    3720
gaataagaac ctggtcatgc tttactcctg tattgttatt ttgttcattt ccaattgatt    3780 ctctacttt ccctttttg tattatgtga ctaattagtt ggcatattgt taaaagtctc    3840
tcaaattagg ccagattcta aaacatgctg cagcaagagg accccgctct cttcaggaaa    3900
agtgttttca tttctcagga tgcttcttac ctgtcagagg aggtgacaag gcagtctctt    3960
gctctcttgg actcaccagg ctcctattga aggaaccacc cccattccta aatatgtgaa    4020
aagtcgccca aaatgcaacc ttgaaaggca ctactgactt tgttcttatt ggatactcct    4080
cttattattt ttccattaaa aataatagct ggctattata gaaaatttag accatacaga    4140
gatgtagaaa gaacataaat tgtccccatt accttaaggt aatcactgct aacaatttct    4200
ggatggtttt tcaagtctat ttttttttcta tgtatgtctc aattctcttt caaaattta    4260 cagaatgtta tcatactaca tatatacttt ttatgtaagc tttttcactt agtattttat    4320
caaatatgtt tttattatat tcatagcctt cttaaacatt atatcaataa ttgcataata    4380
ggcaacctct agcgattacc ataattttgc tcattgaagg ctatctccag ttgatcattg    4440
ggatgagcat ctttgtgcat gaatcctatt gctgtatttg ggaaaatttt ccaaggttag    4500
attccaataa atatctattt attattaaat attaaaatat ctatttatta ttaaaaccat    4560
ttataaggct ttttcataaa tgtatagcaa ataggaatta ttaacttgag cataagatat    4620
gagatacatg aacctgaact attaaaataa aatattatat ttaacccttta gtttaagaag    4680 aagtcaatat gcttatttaa atattatgga tggtgggcag atcacttgag gtcaggagtt    4740
cgagaccagc ctggccaaca tggcaaaacc acatctctac taaaaataaa aaaattagct    4800
gggtgtggtg gtgcactcct gtaatcccag ctactcagaa ggctgaggta caagaattgc    4860
tggaacctgg gaggcggagg ttgcagtgaa ccaagattgc accactgcac tccagccggg    4920
gtgacagagt gagactccga ctgaaaataa ataaataaat aaataaataa ataaataaat    4980
attatggatg gtgaagggaa tggtatagaa ttggagagat tatcttactg aacacctgta    5040
gtcccagctt tctctggaag tggtcgtatt tgagcaggat gtgcacaagg caattgaaat    5100
gcccataatt agtttctcag ctttgaatac actataaact cactggctga aggaggaaat    5160
tttagaagga agctactaaa agatctaatt tgaaaaacta caaaagcatt aactaaaaaa    5220
gtttattttc ctttttgtctg ggcagtagtg aaaataacta ctcacaacat tcactatgtt    5280
tgcaaggaat taacacaaat aaaagatgcc ttttttactta aacaccaaga cagaaaactt    5340
gcccaatact gagaagcaac ttgcattaga gagggaactg ttaaatgttt tcaacccagt    5400
tcatctggtg gatgttttg caggttactc tgagaatttt gcttatgaaa aatcattatt    5460
tttagtgtag ttcacaataa tgtattgaac atacttctaa tcaaaggtgc tatgtccttg    5520
```

```
tgtatggtac taaatgtgtc ctgtgtactt ttgcacaact gagaatcctg cagcttggtt      5580
taatgagtgt gttcatgaaa taaataatgg aggaattgtc a                          5621

<210> SEQ ID NO 3
<211> LENGTH: 21
<212> TYPE: RNA
<213> ORGANISM: Artificial Sequence
<220> FEATURE:
<223> OTHER INFORMATION: Synthetic Construct

<400> SEQUENCE: 3
agaaauucuc gaauguucuu u                                                21

<210> SEQ ID NO 4
<211> LENGTH: 21
<212> TYPE: RNA
<213> ORGANISM: Artificial Sequence
<220> FEATURE:
<223> OTHER INFORMATION: Synthetic Construct

<400> SEQUENCE: 4
uuucuuuaag agcuuacaag a                                                21

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
gaaaacaccc aacctggtca tttc                                             24

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
caccgtgcgg ggtaaaaagc g                                                21

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (21)..(22)
<223> OTHER INFORMATION: Deothymidine

<400> SEQUENCE: 7
ucucugagcg cacuauucat t                                                21

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(19)
```

```
<223> OTHER INFORMATION: Deoxythymidine

<400> SEQUENCE: 8
uauccgucgg ucaucuatt                                                    19

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: Deoxythymidine

<400> SEQUENCE: 9
tctctgagcg cactattcat t                                                 21
```

OPHTHALMIC COMPOSITION COMPRISING WS-12 AND METHODS TO TREAT XEROPHTHALMIA

CROSS-REFERENCE TO RELATED APPLICATIONS

This application is filed under the provisions of 35 U.S.C. §371 and claims the priority of International Patent Application No. PCT/ES2011/070627 filed on 8 Sep. 2011 entitled "Pharmaceutical Composition for the Treatment of Dry Eye" in the name of Carlos BELMONTE MARTINEZ, et al., which claims priority to Spanish Patent Application No. P201031341, filed on 8 Sep. 2010, both of which are hereby incorporated by reference herein in their entirety.

TECHNICAL FIELD OF THE INVENTION

The invention relates to therapeutic compositions for the treatment of dry eye, more specifically to compositions comprising a TRPM8 receptor agonist ligand.

BACKGROUND OF THE INVENTION

Wetness of the ocular surface and other exposed mucosae is maintained by a continuous aqueous fluid secretion produced by exocrine glands. Disturbances of this process lead to eye, mouth and vaginal dryness syndromes that are highly prevalent, particularly among aged persons (Moss, S. E., et al. 2008. Optom. Vis. Sci. 85:668-674; Barker, K. E. & Savage, N. W. 2005. Aust. Dent. J. 50:220-223; Leiblum, S. R., et al. 2009. J. Sex Med 6:2425-2433). In the eye, basal tear flow is adjusted to variations in environmental conditions and blinking rate. Tear flow occurring in the absence of emotional or exogenous irritant stimuli ('basal' tear secretion) is adjusted to variations in environmental conditions and blinking rate (Dartt, D. A. 2009, Prog. Retin. Eye Res. 28:155-177). Tearing also increases markedly upon ocular surface irritation (Acosta, M. C. et al. 2004. Invest Ophthalmol. Vis. Sci. 45:2333-2336). Irritating stimuli are detected by mechanonociceptor and polymodal nociceptor trigeminal nerve endings sensitive to injurious mechanical forces, noxious heat and irritant chemicals, that evoke pain (Belmonte, C., et al. 2004. Exp. Eye Res. 78:513-525) and irritation-induced tearing. However, the neural structures responsible of sensing ocular surface dryness to regulate basal tearing rate remain undefined.

Xerophthalmia or dry eye syndrome is a disease characterised by persistent dryness of the conjunctiva and opacity of the cornea.

Multiple causes can lead to xerophthalmia, which is more common in elderly people. Amongst diseases causing xerophthalmia are found: vitamin A deficit, Sjögren syndrome, rheumatoid arthritis and other rheumatologic diseases, chemical or thermal burns, drugs such as atenolol, chlorpheniramine, hydrochlorothiazide, isotretinoin, ketorolac, ketotifen, levocabastin, levofloxacin, oxybutynin, tolterodine.

Treatments used to treat xherophtalmia include corticosteroids which may be effective in early stages of the disease, vitamine A supplements and pilocarpine which is a drug that increases tear production. Among improve dryness preparations (artificial teras) solutions hypromellose and carbomer ges1 which are applied to the conjunctiva are used. However, these treatments have a clear limitations regarding its efficacy and toxicity. Therefore, there is a need to provide new improved treatments for xherophtalmia, vaginal dryness and dry mouth syndrome.

SUMMARY OF THE INVENTION

In a first aspect the invention relates to the use of a TRPM8 agonist or of combinations thereof for manufacturing a medicament for the treatment or prevention of a disease selected from xerophthalmia, vaginal dryness, and burning mouth syndrome.

In a second aspect, the invention relates to a composition that comprises at least one TRPM8 agonist and at least one drug useful for the treatment of one or more of the diseases selected from xerophthalmia, vaginal dryness, and burning mouth syndrome, and, if desired, a pharmaceutically acceptable vehicle.

In a third aspect, the invention relates to the use of a TRPM8 antagonist for manufacturing a medicament for the treatment of epiphora.

In another aspect, the invention relates to a composition comprising at least one TRPM8 antagonist and at least one drug useful for the treatment of epiphora, and, if desired, a pharmaceutically acceptable vehicle.

DETAILED DESCRIPTION OF THE INVENTION

Figure 1:
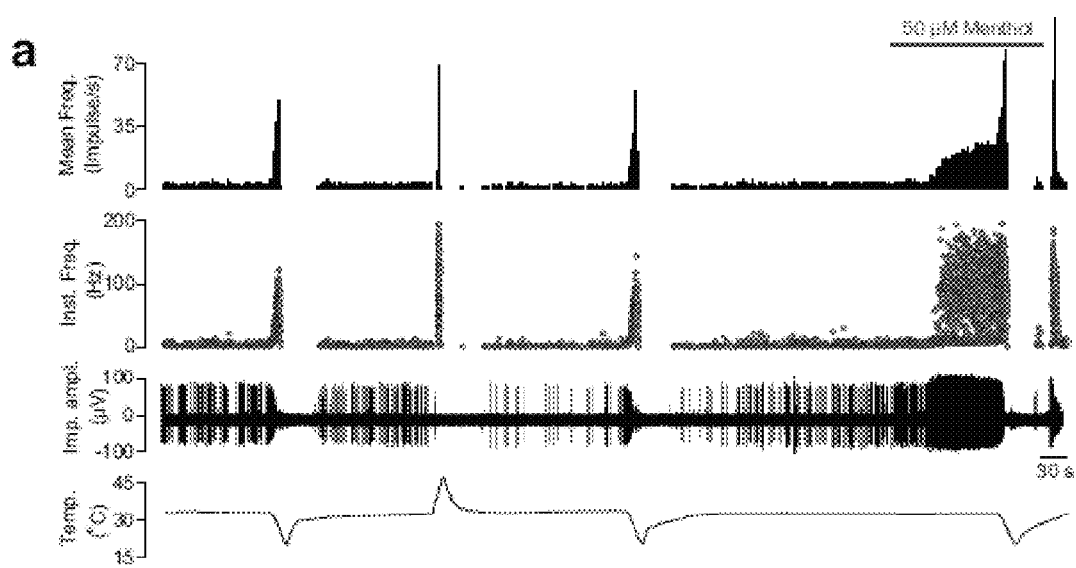
FIG. 1a-f. Response characteristics of cold-sensitive terminals of the mouse cornea. a. nerve terminal impulse (NTI) activity in a cold-sensitive terminal in response to cooling and heating pulses and to menthol. Tracings from top to bottom 25 represent: mean Trigger frequency (Mean freq., Hz) instantaneous frequency (Hz) (Inst. Freq., Hz), direct recording of electrical activity Imp-ampl.µV) (Imp. ampl., en µV), temperature of the perfusion solution (Temp in ° C.) b. Average trigger frequency of 55 cold-sensitive endings (Mean freq., in impulses/s) in response to cooling ramps. Data 3 are mean±SEM. c. Cooling threshold distribution (represented as −~T° c. from basal temperature) of 55 cold-sensitive nerve endings d. Change in trigger frequency versus temperature, determined for the same 55 cold-sensitive endings. For each nerve ending there is shown the frequency change (Mean freq. in implulses/s) and that peak 5 frequency is reached. The tick line represents the average value of each of the 55 individual slopes e. nerve terminal impulse activity in a cold sensitive nerve terminal in response to cooling steps. Tracings show mean trigger frequency frequency (Mean freq., Hz) instantaneous frequency (Hz) (Inst. Freq., Hz), numbers of impulses per burst of potential of action (Impulses/Bursa) and temperature of the perfusion solution (Temp in 10° C.). f. Mean trigger frequency of 10 cold-sensitive terminals during cooling steps. A significant increase in mean trigger frequency rate proportional to the temperature reduction, was observed during the initial period of the cooling step (first 30 s, dynamic response, Pearson correlation coefficient=−0.98, p=0.002) and during the last 30 seconds of the step (static response, Pearson correlation coefficient=−0.96, p=0.014).
Figure 1:
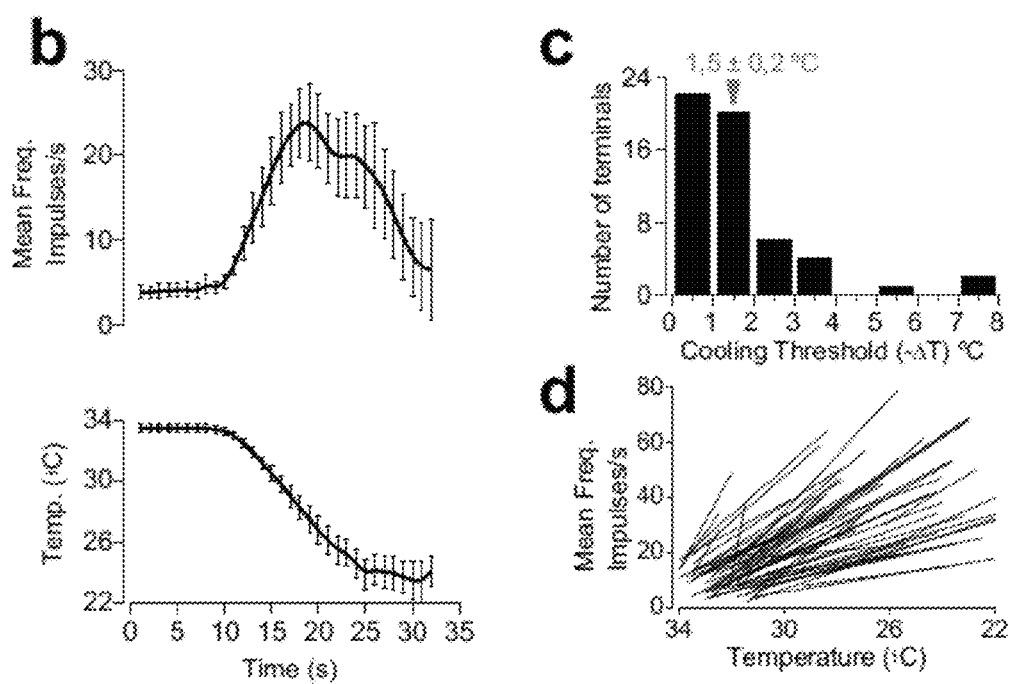
Figure 1:
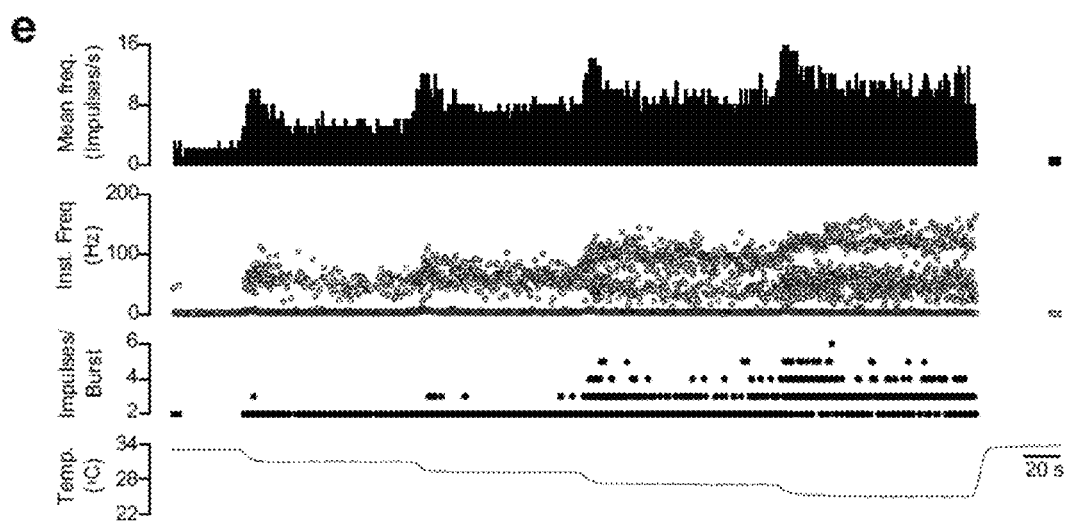
Figure 1:
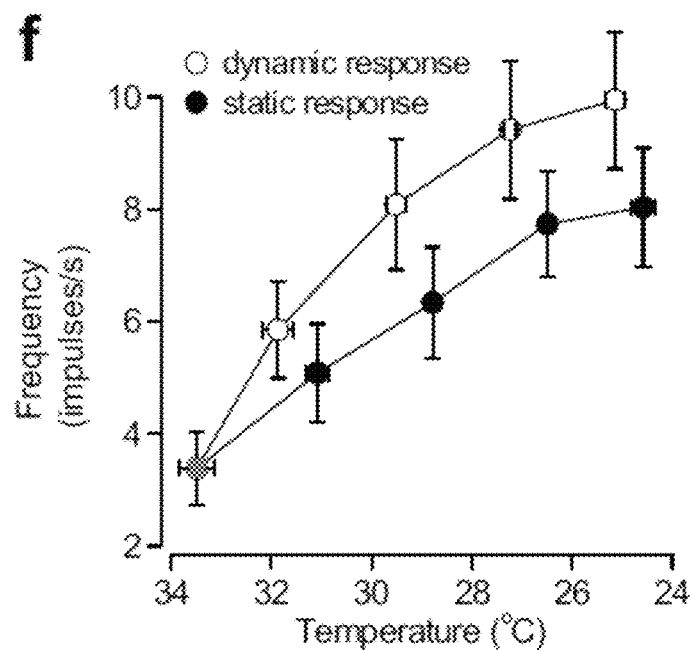

The inventors of this invention have discovered that, surprisingly, the TRPM8 receptor is involved in the control of tearing and that its activation using agonists thereof results in an increased tearing. Specifically, the inventors of this invention have described that cold thermoreceptors innervating the cornea in mammals keep a tonic trigger activity at normal corneal temperature and are markedly sensitive to minor thermal variations in the eye surface, such as those resulting from evaporation of the precorneal tear film that occurs in the intervals between blinking and during exposure to dry environments. This marked cold sensitivity is the result of a high expression of TRPM8 channels, that critically determine a spontaneous basal activity and an increase in the frequency of triggering in response to cold. Furthermore, the inventors have seen that the removal of TRPM8 channels with genetic techniques halves tear secretion in mice. Partial silencing by corneal heating also reduces tear secretion in humans.

Therefore, TRPM8 is a molecular candidate for the detection of moisture in cold thermoreceptor nerve fibres innervating the exposed eye surface in land animals. The data given in this application (see example 1) show that, in thermosensitive corneal endings, TRPM8 is critical for the development of both the spontaneous and cold-induced activity resulting in tear production. Therefore, stimulation of TRPM8 increases the stimulation of tear secretion by cold-sensitive fibres by activation of TRPM8.

Therefore, the present invention relates to the treatment of xerophthalmia, vaginal dryness, and burning mouth syndrome by the use of different therapeutic agents. Furthermore, the results obtained by the authors of the present invention open the way to the treatment of excessive tearing (epiphora) by the use of different agents inhibiting the TRPM8 receptor.

Therapeutic Uses of TRPM8 Agonists

Thus, the present invention relates to the use of a TRPM8 agonist or of combinations thereof for manufacturing a medicament for the treatment or prevention of a disease selected from xerophthalmia, vaginal dryness, and burning mouth syndrome.

The TRPM8 receptor or Transient receptor potential cation channel subfamily M member 8, also known as cold and menthol receptor 1 or CMR1, is a protein that is coded by the TRPM8 gene in humans (Clapham D E, et al. 2005. Pharmacological Reviews 57 (4): 427-50).

TRPM8 is an ion channel that, after activated, allows sodium ions ($Na^+$) and calcium ions ($Ca^{2+}$) to enter the cell, thus generating depolarisation of said cell, leading to a change in the membrane potential.

The TRPM8 protein is expressed in sensory neurons and is activated by cold temperatures (approximately below 26° C.), by chemical agents, such as menthol, and by voltage. TRPM8 is also expressed in the prostate, the lungs, the bladder; its function in these organs is not known.

The human TRPM8 gene is located in chromosome 2 in the 2p37.1 region; and codes for a protein of 1104 amino acids (NP_076985.4, SEQ ID NO: 1) coded by the sequence of nucleotides NM_024080.4 (SEQ IS NO: 2). The TRPM8 gene has six trans-membrane segments, with the C and N terminal ends on the cytoplasmic side. Four subunits tetramerise to form active channels.

The term "TRPM8" as used in that description does not relate only to the human gene and protein, but also to orthologues of other species, such as dog (XP_543296.2), mouse (NP_599013.1), rat (NP_599198.2), etc.

The words "treating" or "treatment" designate both therapeutic and prophylactic treatment or preventive measures, where the object is to prevent or stop (reduce) an unwanted physiological change or disorder, such as dryness of the eyes, vagina, or mouth. For the purpose of this invention, beneficial or wanted clinical outcomes include, without limitation, symptom relief, reduction of disease extent, stabilised pathological condition (specifically not worsened), delayed or stopped disease progression, improved or palliated pathological condition and remission (both partial and total), both detectable and non-detectable. Subjects needing treatment include subjects already suffering the disease or disorder, as well as those susceptible of suffering the disease or disorder or those for whom the disease or disorder should be prevented.

The "treatment method" is defined as the administration to a subject needing this treatment of pharmaceutical composition comprising a TRPM8 agonist according to the invention.

"Xerophthalmia or dry eyes syndrome" is defined in this invention as the disease characterised by persistent dryness of the conjunctiva and opacity of the cornea. Multiple causes can lead to xerophthalmia, which is more common in elderly people. Among the causes and diseases causing xerophthalmia are: vitamin A deficit, Sjögren syndrome, rheumatoid arthritis and other rheumatologic diseases, chemical or thermal burns, drugs such as atenolol, chlorpheniramine, hydrochlorothiazide, isotretinoin, ketorolac, ketotifen, levocabastin, levofloxacin, oxybutynin, tolterodine.

Thus, in a particular embodiment, xerophthalmia is associated with vitamin A deficit, Sjögren syndrome, rheumatoid arthritis and other rheumatologic diseases, chemical or thermal burnings, drugs such as atenolol, chlorphenyramine, hydrochlorothiazide, isotretinoin, ketorolac, ketotifen, levocabastin, levofloxacin, oxybutynin, tolterodine.

"Vaginal dryness" is defined as the reduction in the amount of fluids produced in the vagina. This dryness can cause malaise, such as itching, irritation and burning feeling in the genital area, in addition to pain during sexual relations. This lack of lubrication can be due to organic causes or psychical causes. Among the organic causes, the most common is the insufficient amount of oestrogens, for instance, during menopause. Other causes leading to vaginal dryness are vaginitis, that is the inflammation of vaginal tissues, or diabetes. In the case of women with diabetes where vaginal lubrication can be reduced, in particular those with a defective blood glucose control, this lack of lubrication can be associated with two complications: neuropathy, which can reduce the response to sexual stimulus; and damage to blood vessels, which limits blood flow in the vaginal wall reducing the amount of lubricating flow.

Another factor to be considered is stress, which causes an increase in the release of cortisol in blood, that in turn causes an imbalance in the other hormones. Smoking also interferes with oestrogen functions and, therefore, can reduce vaginal lubrication. A similar effect can occur by the action of alcohol and marijuana. Some hormonal drugs, such as contraceptive pills or the drugs used for the treatment of breast, ovary or uterine cancer, can cause vaginal dryness. Tricyclic antidepressants, some antiulcer agents or some antihypertensives can have as side effect the reduction of vaginal secretion. Other drugs that can also cause this problem are antihistamines.

Thus, in a preferred embodiment, vaginal dryness is associated with an insufficient amount of oestrogens, diabetes, stress or alcohol intake, marijuana or drugs, such as drugs used for the treatment of cancer of the breast, ovary or uterus, which can cause vaginal dryness. Also tricyclic antidepressants, antiulcer agents, antihypertensives or antihistamines.

"Burning mouth syndrome" in this invention means the disease called stomatodynia. This disease is due to multiple causes. Inadequate intake of some vegetables or meat supplying iron, folic acid or vitamin B12 can contribute to deficit anaemia contributing to this burning mouth syndrome. Furthermore, some endocrine diseases, such as hypothyroidism or diabetes, or digestive diseases, such as gastroesophageal reflux, also contribute to it.

Another issue influencing the occurrence of this disease is the chronic use of some drugs such as beta-blockers, antihypertensives, and antidiabetics.

In a preferred particular embodiment, the disease is xerophthalmia.

In the present invention, "TRPM8 receptor agonist" is defined as any molecule binding specifically to the TRPM8 receptor and that, upon binding, can cause an increase in the activity of the TRPM8 channel, i.e., that increases sodium and calcium flow through the channel causing a cell depolarisation. These agonists increase the stimulation of tear secretion by cold-sensitive fibres. There is a great variety of studies available to detect the activity of TRPM8 receptor agonists, such as the whole-cell, patch-clamp electrophysiological tests mentioned in the examples of this invention (see example 1), the calcium microscopy methods (Bodding et al., 2007, Cell Calcium, 42, 618-628) and the methods based on the fluorometric imaging plate reader assay (Behrendt et al., 2004. J. Pharmacol. 141, 737-745), amongst others.

Examples of the TRPM8 receptor agonists adequate for use in this invention include, without limitation, the molecules described in Table 1.

TABLE 1

| TRPM8 agonists | |
|---|---|
| Agonist | Number |
| WS-5<br>Ethyl 3-(p-menthane-3-carboxamide) | 1 |
| CPS369 | 2 |
| CPS368 | 3 |
| CPS125 | 4 |
| Frescolat MGA - 2 Isomer | 5 |

TABLE 1-continued

TRPM8 agonists

| Agonist | Number |
|---|---|
| Frescolat ML | 6 |
| Coolant Agent 10     2S Isomer     2R Isomer | 7 |
| (−)-Isopulegol (Coolact P®) | 8 |
| (+)-cis & (−)-trans p-Menthane-3,8-diol Ratio~62:38 (Coolact 38D®) | 9 |
| (−)-Cubebol | 10 |

TABLE 1-continued

TRPM8 agonists

| Agonist | Number |
|---|---|
| "Hasegawa's Cooling Compound" | 11 |
| "IFF's New GRAS Cooling Material" | 12 |
| Icilin / Unilever Analog<br>Icilin<br>AG-3-5, [1-[2-hydroxyphenyl]-4-[2-nitrophenyl-]-1,2,3,6-tetrahydropyrimidine-2-one] | 13 |
| 5-methyl-4-(1-pyrrolidinyl)-3-[2H]-furanone | 14 |
| "Faintly mint-like"<br>4,5-dimethyl-3-(1-pyrrolidinyl)-2-[5H]-furanone | 15 |

TABLE 1-continued

TRPM8 agonists

| Agonist | Number |
|---|---|
| 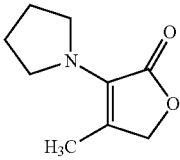<br>4-methyl-3-(1-pyrrolidinyl)-2-[5H]-furanone | 16 |
| 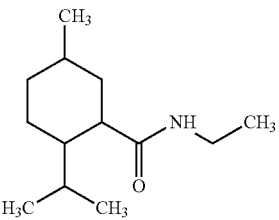<br>WS-3　　　　　　1R,3R,4S-WS-3<br>N-ethyl-p-menthane-3-carboxamide | 17 |
| 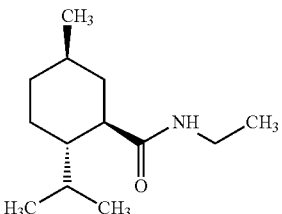<br>WS-11<br>2-isopropyl-5-methyl-cyclohexanecarboxylic acid<br>(2-hydroxy-1,1-dimethyl-ethyl)-amide | 18 |
| 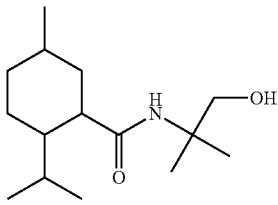<br>WS-12<br>2-isopropyl-5-methyl-cyclohexanecarboxylic acid<br>(4-methoxyphenyl)-amide | 19 |
| 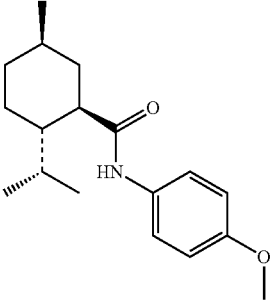<br>WS-14<br>2-isopropyl-5-methyl-cyclohexanecarboxylic acid<br>tert-butylamide | 20 |

TABLE 1-continued

| TRPM8 agonists | |
|---|---|
| Agonist | Number |
| WS-23<br>2-isopropyl-N-2,3-trimethyl butyramide | 21 |
| WS-30<br>2-isopropyl-5-methyl-cyclohexanecarboxylic acid ester 2,3-dihydroxy-propyl | 22 |
| WS-148<br>1-(di-sec-butyl-phosphinoyl)-heptane | 23 |
| − Menthol    + Menthol | 24 |
| Geraniol | 25 |
| Linallol | 26 |

TABLE 1-continued

TRPM8 agonists

| Agonist | Number |
|---|---|
| 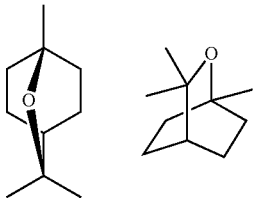 Eucalyptol | 27 |
| 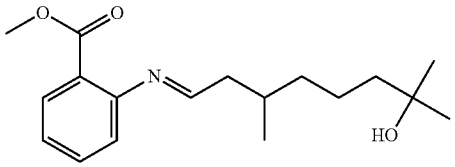 Hydroxyl-citronellal | 28 |
| 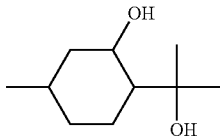 PMD-38 p-menthane-3,8-diol | 39 |
| TRPM8 specific agonist antibodies | 30 |
| Constitutively active variants of TRPM8 | 31 |

TABLE 2

Summary of TRPM8 agonists

| Compound | EC$_{50}$ (μM) | Method |
|---|---|---|
| Icilin | 0.2 ± 0.1$^a$ | FL |
|  | 1.4$^b$ | CI |
|  | 0.50$^c$ | EP |
|  | 0.36 ± 0.03$^d$ | EP |
| Menthol | 10.4$^b$ | CI |
|  | 83.6 ± 0.04$^c$ | EP |
|  | 66.7 ± 3.3$^d$ | EP |
| WS-12 | 0.193$^b$ | CI |
|  | 0.680$^b$ | EP |
|  | 0.039$^c$ | EP |
| WS-3 | 3.7 ± 1.7$^a$ | FL |
| WS-148 | 4.1$^b$ | CI |
| WS-30 | 5.6$^b$ | CI |
| WS-11 | 6.25$^c$ | EP |
| WS-14 | 21.19$^c$ | EP |
| WS-23 | 44 ± 7.3$^a$ | FL |
| CPS-113 | 1.2$^b$ | CI |
| CPS-369 | 3.6$^b$ | CI |
| Frescolat ML | 3.3 ± 1.5$^a$ | FL |
| Frescolat MGA | 4.8 ± 1.1$^a$ | FL |
| Cooling Agent 10 | 6 ± 2.2$^a$ | FL |
| PMD-38 | 31 ± 1.1$^a$ | FL |
| Geraniol | 5900 ± 1600$^a$ | FL |
| Linalool | 6700 ± 2000$^a$ | FL |
| Eucalyptol | 7700 ± 2000$^a$ | FL |
|  | 3400 ± 400$^d$ | EP |
| Hydroxyl-citronellal | 19600 ± 2200$^a$ | FL |

Table 2: Potency in the activation of TRPM8 channels of different chemical agonists measured using calcium microscopy (CI), "fluorometric imaging plate reader assay" (FL) or patch-clamp electrophysiology (EP).
Data obtained from:
$^a$(Behrendt et al., 2004. J. Pharmacol. 141, 737-745.);
$^b$(Bodding et al., 2007 Cell Calcium, 42, 618-628);
$^c$(Beck et al., 2007 Cell Calcium, 41, 285-294..);
$^d$(McKemy et al., 2002. Nature, 416, 52-58.).

In a particular embodiment, the agonist used in the first use of the invention is an agonist selected from WS-5 (Ethyl 3-(p-menthane-3-carboxamide), CPS369, CPS368, CPS125, Frescolat MGA-2 Isomer, Coolant Agent 10, (−)-Isopulegol (Coolact P®), (+)—cis & (−) trans p-Menthane-3,8-diol Ratio ~62:38 (Coolact 38D®), (−)Cubebol, "Hasegawa's Cooling Compound", "IFF's New GRAS Cooling Material", Icilin, 5-methyl-4-(1-pyrrolidinyl)-3-[2H]-furanone, 4,5-dimethyl-3-(1-pyrrolidinyl)-2-[5H]-furanone, 4-methyl-3-(1-pyrrolidinyl)-2-[5H]-furanone, N-ethyl-p-menthane-3-carboxamide, WS-11 (2-isopropyl-5-methyl-cyclohexanecarboxylic acid (2-hydroxy-1,1-dimethyl-ethyl)-Amide), WS-12 (2-isopropyl-5-methyl-cyclohexanecarboxylic acid (4-methoxyphenyl)-amide), WS-14 (2-isopropyl-5-methyl-cyclohexanecarboxylic acid tert-butylamide), WS-23 (2-isopropyl-N-2,3-trimethylbutyramide), WS-30 (2-isopropyl-5-methyl-cyclohexanecarboxylic acid ester 2,3-dihydroxy-propyl), WS-148 (1-(di-sec-butyl-phosphinoyl)-heptane), Menthol, Geraniol, Linallol, Eucalyptol, Hydroxyl-citronellal, PMD-38 (p-menthane-3,8-diol), specific TRPM8 agonist antibodies and constitutively active variants of TRPM8, or combinations thereof.

In a preferred embodiment, the agonist used in the first use of the invention is an agonist different from menthol or a derivative thereof. Therefore, in a preferred embodiment the TRPM8 agonist is selected from icilin, AG3-5, WS-23, WS-148, hydroxyl-citronellal, 5-methyl-4-(1-pyrrolidinyl)-3 [2H]-furanone; 4,5-methyl-3-(1-pyrrolidinyl)-2-[5H]-furanone and 4-methyl-3-(1-pyrrolidinyl)-2-[5H]-furanone.

In a more preferred embodiment, the agonist used in the first use of the invention is a specific TRPM8 agonist selected from compounds 1 to 4 of Table I (WS-5, CPS369, CPS368, CPS125), compound 19 (WS-12, Becka B. 2007, Cell Calcium 41(3):285-294) and TRPM8 agonist antibodies.

In another preferred embodiment, the agonist is selected from those with an $EC_{50}$ lower than 7 (see Table II) such as Cooling Agent 10, Frescolat MGA, Frescolat ML, CPS-369, CPS-113, WS-23, WS-11, WS-30, WS-148, WS-3, WS-12 and Icilin.

A "specific agonist" is defined in this invention as the agonists activating TRPM8 without activating other channels of the same family or activating TRPM8 with an efficacy of at least 50, 100, 1000, 2000 times more than the other channel of the same family.

The methods that can be used to measure the specificity of a TRPM8 agonist are similar to those previously described to measure the agonist activity of a compound, such as electrophysiological methods, calcium microscopy methods, etc.

TRPM8 Receptor Agonist Antibodies

A TRPM8 agonist for use in the present invention can be a TRPM8 agonist antibody or a fragment thereof that can bind specifically to the TRPM8 receptor and more particularly to the extracellular domain of this receptor and induce its activation. The agonist antibody can bind specifically and activate the human TRPM8 receptor or an orthologue of the homologous TRPM8 receptor.

Therefore, in a particular embodiment, the TRPM8 receptor agonist is a TRPM8 anti-receptor agonist antibody, which can be of any class or subclass of immunoglobulins, such as IgG, IgM, IgA, IgD and IgE. In a particular embodiment, at least one of these TRPM8 anti-receptor agonist antibodies is a type IgG-2A immunoglobulin.

In this invention, the word "antibody" must be interpreted broadly and includes polyclonal, monoclonal, multispecific antibodies and fragments thereof (F(ab')$_2$, Fab), provided that they can recognise the relevant antigen, able to bind specifically to the TRPM8 receptor or to the extracellular domain of this receptor. Examples of antibodies that can be used within this invention are for instance and without limitation, polyclonal antibodies, monoclonal antibodies, recombinant antibodies, chimerical antibodies, humanised antibodies, fully human antibodies, etc.

In the present invention, a "TRPM8 receptor agonist antibody" is defined as any antibody that can bind specifically to the TRPM8 receptor or to the extracellular domain of this receptor, and induce activation of the channel so that an increase is generated in sodium and calcium flow through the channel. Methods adequate for the detection of an agonist antibody are based on the ability to activate TRPM8 as described in detail above within the therapeutic uses of the agonists according to the invention.

Polyclonal antibodies are originally heterogeneous mixtures of antibody molecules produced in the serum of animals immunised with an antigen. They also include monospecific polyclonal antibodies obtained from the heterogeneous mixtures, for instance, by column chromatography with peptides of a single epitope of the relevant antigen.

A monoclonal antibody is a homogeneous population of antibodies specific for a single epitope of the antigen. These monoclonal antibodies can be prepared by conventional techniques already described, for instance in Köhler and Milstein [Nature, 1975; 256:495-397] or Harlow and Lane ["Using Antibodies. A Laboratory Manual" from E. Harlow and D. Lane, Editor: Cold Spring Harbor Laboratory Press, Cold Spring Harbor, N.Y.; 1998 (ISBN 978-0879695439)].

A chimerical antibody is a monoclonal antibody built by cloning or recombination of antibodies from different animal species. In a typical, but not limiting, structure of the invention, the chimerical antibody includes a part of a monoclonal antibody, generally the variable region (Fv), that includes the sites for recognition and binding to the antigen, and the other part corresponds to a human antibody, generally the part including the constant region and the adjacent constant.

A fully human antibody is an antibody or antibodies that have been produced in transgenic animals with human immune system or by immunisation in vitro of human immune cells (including both genetic and traditional immunisation with or without adjuvants and pure antigen or not; or by any method of antigen exposure to the immune system) or by native/synthetic libraries produced from human immune cells. These antibodies can be obtained and selected from transgenic animals (for instance, mice) where genes of human immunoglobulins have been cloned and are immunised with the target antigen (in this invention with the TRPM8 receptor). These antibodies can be obtained by selection of single-chain (scFv) or antigen binding (Fab) variable human regions given in phage display and subsequent cloning and grafting in a human antibody or by any other production and display method known by a person skilled in the art, of the libraries generated by cloning of the variable regions of both chains and subsequent combination/mutation thereof to generate antibody libraries.

A humanised antibody is a monoclonal antibody constructed by cloning and grafting of the hypervariable regions determining complementariness (CDR) of a murine monoclonal antibody in a human antibody in substitution of its own CDR hypervariable regions.

Therefore, in a particular embodiment of the composition of the invention, at least one TRPM8 anti-receptor agonist antibody is a humanised antibody.

Examples of agonist antibodies specific for the TRPM8 receptor have been described by Mahieu F et al. (2007. J Biol Chem 282(5):3325-36.) and by Obata K et al. (2005. J Clin Invest. 115(9):2393-2401).

Additionally, in the context of this invention, the term "antibody" also includes variants with an impaired glycosylation pattern, as described in WO2006088447, as well as antibody fragments, obtained from the protein or by recombinant technology, glycated or non-glycated, that can consist (i) of variable areas of the antibodies bound to each other by a binding peptide (scFv), (ii) in the variable area together with the CH1 constant of the heavy chain (Fd) bound to the light chain by cysteines or by binding peptides and disulphur bond (scFab), (iii) new variants, such as heavy chains alone, or (iv) any modification made of the antibody fragments for the purpose of making them more akin, less immunogenic (humanised) or more stable in biological fluids and with the ability to cause activation of the TRPM8 receptor.

The TRPM8 receptor agonist antibodies described in this invention can be obtained by conventional techniques of genetic or recombinant engineering, of antibody production, of extraction and purification from fluids or biological tissues, or by any other conventional technique for obtaining proteins and antibodies which are widely known by a person skilled in the art. When the TRPM8 receptor agonists are antibodies, for producing them the following may be used, without this involving any limitation, among others: immunisation techniques in animals, including transgenic animals for human immunoglobulin genes, production of monoclonal antibodies by hybridomas, production by antibody libraries, that can be native, synthetic or derived from immunised organisms against the relevant antigen and that could be selected by very different display methods (phage display, ribosome display, etc.) and subsequently by genetic engineering techniques could be redesigned and expressed in vectors designed for the production of recombinant antibodies of different sizes, composition, and structure. A review of the main methods for the production and purification of the antibodies can be found, for instance, in:

"Handbook of Therapeutic Antibodies", of S. Dübel. Publisher: Wiley-VCH, 2007, Vol: I a III (ISBN 978-3527314539);

"Antibodies: Volume 1: Production and Purification" of G. Subramanian Ed., Publisher: Springer, 1st Ed, 2004 (ISBN 978-0306482458);

"Antibodies: Volume 2: Novel Technologies and Therapeutic Use", of G. Subramanian Ed., Publisher: Springer, first edition, 2004 (ISBN 978-0306483158);

"Molecular Cloning: a Laboratory manual", of J. Sambrook and D. W. Russel Eds., Publisher: Cold Spring Harbor Laboratory Press, third edition, 2001 (ISBN 978-0879695774).

More specifically, for producing and obtaining antibodies binding specifically to the TRPM8 receptor any of the methods described in WO98/16249, WO2004/010947, US2004/0109847 and US2005/0013811 can be used, with the content included completely as reference.

Constitutively Active Variants of TRPM8

In the present invention the TRPM8 agonists also include constitutively active variants of the TRPM8 receptor or a functionally equivalent variant thereof.

"Constitutively active variants of the TRPM8 receptor" are defined as the peptide sequences derived from the TRPM8 sequence that, when expressed in a cell, causes that mixed TRPM8 channels formed by subunits of native TRPM8 and of this constitutively active variant result in continuously activated channels. The definition of "functionally equivalent variant of a constitutively active variant of the TRPM8 receptor" is defined in this invention as any polypeptide whose sequence that can be obtained by insertion, substitution or deletion of one or more amino acids of the sequences of the sequence of constitutively active variants of the TRPM8 receptor and keeping at least in part the ability to form constitutively activated channels. To establish whether a channel is constitutively active, electrophysiological techniques such as those mentioned above can be used. Preferably, the variants of the natural ligand of 4-1BB have a sequence identity with this ligand of at least 50%, at least 60%, at least 70%, at least 80%, at least 90%, at least 91%, at least 92%, at least 93%, at least 94%, at least 95%, at least 96%, at least 97%, at least 98%, or at least 99%. The determination of the identity degree between the variants and the natural ligand is performed using methods and computer algorithms well known to a person skilled in the art. Preferably, the identity between two amino acid sequences is determined using the algorithm BLASTP (BLAST Manual, Altschul, S., et al, NCBI NLM NIH Bethesda, Md. 20894, Altschul, S., et al., J. Mol. Biol. 21 5: 403-410 (1990).

A person skilled in the art will understand that mutations in the nucleotide sequence of the functionally equivalent variant of a constitutively active variant of the TRPM8 receptor leading to conservative substitutions of amino acids in positions not critical for protein functionality, are evolutively neutral mutations not affecting its global structure or its functionality.

First Composition of the Invention

As understood by a person skilled in the art, TRMP-8 agonists can be used in combination with other drugs useful for the treatment of xerophthalmia, vaginal dryness and burning mouth syndrome. Therefore, in a another aspect, the invention relates to a composition that comprises at least one TRPM8 agonist and at least one drug useful for the treatment of one or more of the diseases selected from xerophthalmia, vaginal dryness, and burning mouth syndrome, and, if desired, a pharmaceutically acceptable vehicle.

The TRPM8 agonists adequate for use in the compositions of this invention and the pharmaceutically acceptable vehicles have been described previously.

Medicaments useful for the treatment of xerophthalmia are, amongst others, corticoids, vitamin A, pylocarpine, hypromellose solutions, carbomer gels, cyclosporine, lubricant drops containing glycerol, hydroxypropyl methylcellulose, hydroxymethyl cellulose, carboxymethyl cellulose, polyethylene glycol, polyvinyl alcohol, hyaluronic acid, castor oil, and mineral oil.

Medicaments useful for the treatment of vaginal dryness include, amongst others, lubricants of water base, vitamin E, oestrogens, aglycon isoflavones, hyaluronic acid, selective modulators of the oestrogen receptor, such as raloxifen, etc.

Medicaments useful for the treatment of burning mouth syndrome include, among others, capsaicin, nystatin (Mycostatin) or fluconazole (Diflucan), anticonvulsivants such as gabapentin (Neurontin), sedatives in the family of benzodiazepines, such as clonazepam (Klonopin), antidepressants, antiepileptics and anticonvulsivants, such as amitriptyline, carbamazepine, Mexiletine, Lamotrigine, phenyloin, N-phenylethyl amitriptyline, Desipramine, Gabapentin, or nortriptyline (Pamelor, Aventyl).

As used in this document, a "pharmaceutically acceptable vehicle" includes additives, such as preservatives, excipients, loads, wetting agents, binding agents, disintegrating agents, buffers that can be present in the compositions of the invention. These additives can be, for instance, magnesium and calcium carbonates, carboxymethyl cellulose, starches, sugars, gums, magnesium or calcium stearate, colouring matters, or flavouring agents. There is a high variety of pharmaceutically acceptable additives for pharmaceutical dosage forms and the selection of appropriate additives is a routine matter for the skilled in the art of pharmaceutical formulation.

In another embodiment, the invention relates to the use of a first composition of the invention for the manufacturing of a medicament for the treatment of one or more of the diseases selected from xerophthalmia, vaginal dryness and burning mouth syndrome.

In another embodiment, the invention relates to a first composition of the invention for the treatment of one or more of the diseases selected from xerophthalmia, vaginal dryness and burning mouth syndrome.

In another embodiment, the invention relates to a method for the treatment of one or more of the diseases selected from xerophthalmia, vaginal dryness and burning mouth syndrome in a subject comprising the administration to this subject of a first composition of the invention.

The administration of the composition of the invention can be performed by different routes, for instance, intravenous, intraperitoneal, subcutaneous, intramuscular, topical, intradermal, intranasal or intrabronchial, and it can be administered locally or systemically or directly to the target site. A review of the different administration routes of active substances, of the excipients to be used and the manufacturing procedures can be found in *Tratado de Farmacia Galenica*, C. Faullí i Trillo, Luzán 5, S. A. de Ediciones, 1993 and in *Remington's Pharmaceutical Sciences* (A. R. Gennaro, Ed.), 20th edition, Williams & Wilkins PA, USA (2000).

The dosage regimen will be established by the physician and the clinical factors. As it is well known in medicine, the dosages depend on many factors, including the physical characteristics of the patient (age, size, sex), the administration route used, the severity of the disease, the particular compound used and the pharmacokinetic properties of the subject.

The composition of the invention can contain an amount of TRPM8 agonist agents that can vary within a wide range, but always at therapeutically effective amounts.

In this invention a "therapeutically effective amount" is defined as the amount of a TRPM8 receptor agonist sufficient to cause an increase in tearing, vaginal secretion or salivary secretion in the patient.

Therefore, the composition of the invention can contain an amount of TRPM8 receptor agonist ranging from 0.1 to 2,000 mg, preferably within the range from 0.5 to 500 mg and, even more preferably, from 1 to 200 mg. Appropriate doses of the compositions can range from 0.01 to 100 mg/kg of body weight, preferably from 0.1 to 50 mg/kg of body weight, more preferably, from 0.5 to 20 mg/kg of body weight. The composition can be administered a variable number of times a day, in particular from 1 to 4 four doses a day.

As a person skilled in the art understands, both the TRPM8 agonist and the drug useful for the treatment of one or more diseases selected from xerophthalmia, vaginal dryness and burning mouth syndrome can be present in a pharmaceutically acceptable vehicle.

Excipients or vehicles preferred for use in this invention include sugars, starches, celluloses, gums, and proteins. In a particular embodiment, the pharmaceutical composition of the invention will be formulated in a solid (e.g., tablets, capsules, lozenges, granules, suppositories, sterile crystalline or amorphous solids that can be reconstituted to provide liquid forms etc.), liquid (for instance, solutions, suspensions, emulsions, elixirs, lotions, ointments, etc.) or semisolid (gels, ointments, creams, and similar) pharmaceutical dosage form. The pharmaceutical compositions of the invention can be administered by any route, including, but not limited to, oral, intravenous, intramuscular, intraarterial, intramedullary, intrathecal, intraventricular, transdermal, subcutaneous, intraperitoneal, intranasal, enteric, topical, sublingual or rectal. A review of the different administration routes of active substances, of the excipients to be used and the manufacturing procedures can be found in *Tratado de Farmacia Galénica, C. Faullí i Trillo, Luzán* 5, S. A. de Ediciones, 1993 and in *Remington's Pharmaceutical Sciences* (A. R. Gennaro, Ed.), 20th edition, Williams & Wilkins PA, USA (2000).

As a person skilled in the art understands, the composition of the invention comprising at least one TRPM8 receptor agonist will be formulated according to the administration route to be used. Therefore, in a particular embodiment, the composition of the invention comprising at least one TRPM8 receptor agonist will be formulated adequately for ophthalmic administration.

In another particular embodiment, the composition of the invention comprising at least one TRPM8 receptor agonist will be formulated adequately for vaginal administration.

In another particular embodiment, the composition of the invention comprising at least one TRPM8 receptor agonist will be formulated adequately for mouth administration.

In a particular embodiment, the agonist used in the first use of the invention is an (Coolact 38D®), (−)-Cubebol, "Hasegawa's Cooling Compound", "IFF's New GRAS Cooling Material", Icilin, 5-methyl-4-(1-pyrrolidinyl)-3-[2H]-furanone, 4,5-dimethyl-3-(1-pyrrolidinyl)-2[5H]-furanone, 4-methyl-3-(1-pyrrolidinyl)-2 [5H]-furanone, N-ethyl-p-menthane-3-carboxamide, WS-11 (2-isopropyl-5-methyl-cyclohexanecarboxylic acid (2-hydroxy-1,1-dimethyl-ethyl acid)-Amide), WS-12 (2-isopropyl-5-methyl-cyclohexanecarboxylic acid (4-methoxyphenyl)-amide), WS-14 (2-isopropyl-5-methyl-cyclohexanecarboxylic tert-butylamide), WS-23 (2-isopropyl-N-2,3-trimethylbutyramide), WS-30 (2-isopropyl-5-methyl-cyclohexanecarboxylic acid ester 2,3-dihydroxy-propyl), WS-148 (1-(di-sec-butyl-phosphinoyl)-heptane), Menthol, Geraniol, Linallol, Eucalyptol, Hydroxyl-citronellal, PMD-38 (p-menthane-3,8-diol), Agonist antibodies specific for TRPM8 and constitutively active variants of TRPM8, or combinations thereof.

In a preferred embodiment, the agonist used in the first use of the invention is not menthol or a derivative thereof. Therefore, in a preferred embodiment the TRPM8 agonist is selected from icilin, AG3-5, WS-23, WS-148, hydroxyl-citronellal, 5-methyl-4-(1-pyrrolidinyl)-3 [2H]-furanone; 4,5-methyl-3-(1-pyrrolidinyl)-2-[5H]-furanone and 4-methyl-3-(1-pyrrolidinyl)-2-[5H]-furanone. In a more preferred embodiment, the agonist used in the first use of the invention is a specific TRPM8 agonist selected from: compounds 1 to 4 of table I (WS-5, CPS369, CPS368, CPS125), compound 20 (WS-12, Becka B. 2007, Cell Calcium 41(3):285-294) TRPM8 agonist antibodies.

In another preferred embodiment, the agonist is selected from those with an $EC_{50}$ lower than 7 (see Table 2) such as the Cooling Agent 10, Frescolat MGA, Frescolat ML, CPS-369, CPS-113, WS-23, WS-11, WS-30, WS-148, WS-3, WS-12 and Icilin.

As understood by a person skilled in the art, in the event the TRPM8 agonist is an antibody or a constitutively active variant of TRPM8, another method to implement this invention is the administration of a vector comprising the nucleotide sequences encoding these TRPM8 receptor agonists.

The nucleotide sequence encoding these agonists can be cloned preceded by regulatory sequences of expression and operatively bound to them. As used in this description, the expression "operatively bound" means that the nucleotide sequences are within the adequate reading framework for expression under the control of these regulatory sequences.

The regulatory sequences of value for this invention can be nuclear promoter sequences or, alternatively, enhancer sequences and/or other regulatory sequences increasing the expression of the heterologous sequence of nucleic acid. The promoter can be constitutive or inducible. If a constant expression of the heterologous sequence of nucleic acid is wanted, a constitutive promoter is then used. Examples of well-known constitutive promoters include the early immediate promoter of cytomegalovirus (CMV), promoter of Rous sarcoma virus, and similar. Many other examples of constitutive promoters are well known in the art and can be used in the practice of the invention. If the controlled expression of the heterologous sequence of nucleic acid is wanted, an inducible promoter must be then used. In a non-induced state, the inducible promoter is "silent". "Silent" means that, in the absence of an inducer, low or no expression of the nucleic acid heterologous sequence is detected; in the presence of an inducer, however, expression of the nucleic acid heterologous sequence occurs. The expression level can be often controlled modifying the concentration of the inducer. Controlling the expression, for instance modifying the concentration of the inducer so that an inducible promoter is stimulated more strongly or more weakly, the concentration of the product transcribed of the nucleic acid heterologous sequence can be affected. In case the nucleic acid heterologous sequence codes a gene, the amount of protein synthesised can be controlled. Therefore, the concentration of therapeutic product can be modified. Examples of well-known inducible promoters are: a promoter of oestrogen or androgen, a promoter of metallothionein, or a promoter responding to ecdysone. Many other examples are well known in the art and can be used in the practice of the invention. In addition to the constitutive and inducible promoters (that usually perform in a high number of types of cells or tissues), specific tissue promoters can be used to reach the expression of the heterologus sequence of nucleic acid specific in cells or tissues. Well-known examples of specific tissue promoters include several specific muscle promoters, including: the promoter of skeletal α-actin, the promoter of cardiac actin, promoter of skeletal troponin C, promoter of cardiac troponin C of slow contraction, and the promoter/enhancer of creatine kinase. There are multiple specific muscle promoters that are well known in the art and can be used in the practice of the invention (for a review in specific muscle promoters see Miller et al., (1993) *Bioessays* 15: 191-196).

In a particular embodiment, TRMP8 agonist antibody is an immunoglobulin of IgG-2A type.

In another particular embodiment, TRMP8 agonist antibody is a humanised antibody.

Furthermore, the possibility that the vector contains a polynucleotide encoding a constitutively active variant of TRPM8 receptor is considered. Therefore, when the vector is expressed in the receptor organism, it will produce the relevant proteins that will cause the aforementioned therapeutic effect discussed for the treatment of diseases, such as xerophthalmia, vaginal dryness, and burning mouth syndrome.

In the scope of the present invention, preferably the vector used is a viral or non-viral vector adequate for use in gene therapy; by way of illustration, but not limiting, these vectors can be viral vectors based on retrovirus, adenovirus, etc., or in the case of non-viral vectors, they can be DNA-liposome, DNA-polymer, DNA-polymer-liposome, etc., complexes. [see "Nonviral Vectors for Gene Therapy", published by Huang, Hung and Wagner, Academic Press (1999)]. These viral and non-viral vectors containing the sequence encoding the TRPM8 agonist can be administered directly into the human or animal body by conventional methods. Alternatively, these vectors can be used to transform, transfect or infect cells, for instance, cells of mammals, including humans, ex vivo, and subsequently implant them in the human or animal body to obtain the intended therapeutic effect. For administration to the subject, these cells will be formulated in an adequate medium not affecting adversely their viability.

Second Therapeutic Use of the Invention

In another aspect, the invention relates to the use of a TRPM8 antagonist or combinations thereof to manufacture a medicament for the treatment or prevention of epiphora.

In another aspect the invention relates to a TRPM8 antagonist or combinations thereof for use in the treatment or prevention of epiphora.

In another aspect the invention relates to a method for the treatment of epiphora in a subject comprising the administration to this subject of a TRPM8 antagonist or combinations thereof.

The words "TRPM8", "treatment" and "prevention" have been previously described in the context of the first use of the invention.

In this invention "epiphora" is defined as the existence of continuous, excessive tearing. This excessive tear production can be caused by an external stimulus acting as irritant, for instance exposure to cold, contaminated environments, chemical substances, foreign bodies or ulcers in the cornea. Epiphora can be also caused by conditions causing inflammation of the eye surface, for instance acute conjunctivitis.

Other times, the cause is a defect in the tear drainage system, due to an abnormal position of the eyelid (ectropion) or obstruction in the nasolacrimal duct or the lacrimal sac. The obstruction of the lacrimal system can be congenital if present since birth, in this case the most common is that it is due to imperforation of the nasolacrimal membrane. When it occurs in adults, it can be due to infection of the lacrimal sac or dacryocystitis. Sometimes the origin of epiphora is facial nerve palsy, that causes weakness in the orbicular muscle of eyelids. Other causes of epiphora are: Graves-Basedow disease, Ackerman syndrome, allergies to animals, pollen, etc., bacterial conjunctivitis and blepharitis.

Therefore, in a particular embodiment, epiphora is associated with a disease selected from: Graves-Basedow disease, corneal ulcers, Ackerman syndrome, allergies (animals, pollen, etc), bacterial conjunctivitis, blepharitis, facial nerve palsy, ectropion or obstruction of the nasolacrimal duct or lacrimal sac.

In a particular embodiment, this medicament reduces stimulation of tear secretion by cold-sensitive fibres by means of TRPM8 inactivation.

In the present invention, "TRPM8 receptor antagonist" is defined as any molecule binding specifically to the TRPM8 receptor and that upon binding can cause a decrease in the activity of the TRPM8 channel, i.e., that decreases sodium and calcium flow through the channel causing a cell repolarisation.

Methods adequate to detect whether a given compound is a TRPM8 antagonist are consistent with those described to detect the activity of the TRPM8 receptor agonists described in the context of the first use of the invention.

Table 3 shows illustrative, non-limiting examples of TRPM8 antagonists that can be used in this invention. In addition, the compounds described in the international patent application WO2010/021882 can be used.

TABLE 3

TRPM8 antagonists

| Antagonist | Number |
| --- | --- |
| Antisense oligonucleotide specific for the sequence of the gene encoding TRPM8 | 1 |
| DNA enzyme specific for the TRPM8 sequence | 2 |
| MicroRNA specific for the gene encoding TRPM8 | 3 |
| Ribozyme specific for the sequence of gene encoding TRPM-8. | 4 |
| Interference RNA specific for the sequence of the gene encoding TRPM8<br>5'-AGAAAUUCUCGAAUGUUCUUU-3' (sense) (SEQ ID NO: 3)<br>3'-UUUCUUUAAGAGCUUACAAGA-5' (antisense) (SEQ ID NO: 4)<br>siRNAs for human TRPM-8. Described in Zhang L. et al. (2004. Cancer Research 64: 8365-8373).<br>5'-GAAAACACCCAACCTGGTCATTTC-3' (sense) (SEQ ID NO: 5)<br>5'-CACCGTGCGGGGTAAAAAGCG-3' (antisense) (SEQ ID NO: 6)<br>siRNAS for the sequences of positions 894 and 2736 (exons 8 and 21):<br>5'-UCUCUGAGCGCACUAUUCA(dTdT)-3' (sense) (SEQ ID NO: 7)<br>5'-UAUCCGUCGGUCAUCUA(dTdT)-3' (sense) (SEQ ID NO: 8)<br>5'-TCTCTGAGCGCACTATTCA(dTdT)-3' (SEQ ID NO: 9)<br>Position 894-912 of the TRPM8 sequence (NM_024080.3), described in Thebault et al. (2005. Chemistry, 280: 39423-39435.) | 5 |
| Peptide with ability to bind specifically to TRPM8 and inhibit its activity | 6 |
| Antibody with ability to bind specifically to TRPM8 and inhibit the activity of this channel | 7 |

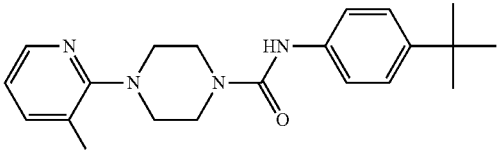

BCTC

N-(4-tert-butyl-phenyl)-4-(3-chloropyridin-2-yl) tetrahydropyrazine-1(2H)-carboxamide

8

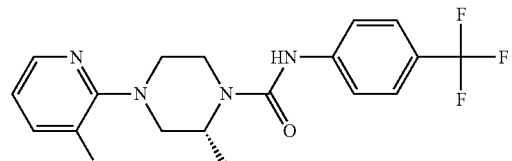

CTPC (2R)-4-(3-chloro-2-pyridinyl)-2-methyl-N-[4-(trifluoromethyl)phenyl]-1-pyperazine-carboxamide

9

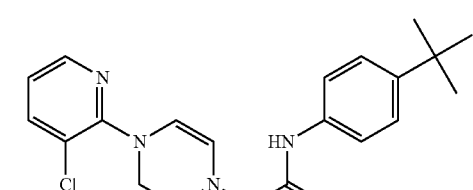

thio-BCTC

N-(4-tert-butyl-phenyl)-4-(3-chloropyridin-2-yl) tetrahydropyrazine-1(2H)-(thio)carboxamide

10

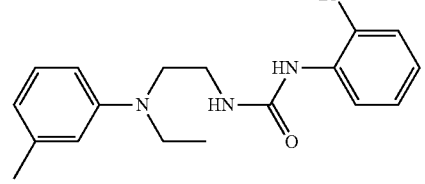

SB-452533

N-(2-bhromophenyl)-N'-(2-[ethyl(3-methylphenyl)amino]ethyl)urea

11

TABLE 3-continued
| TRPM8 antagonists | |
|---|---|
| Antagonist | Number |
| 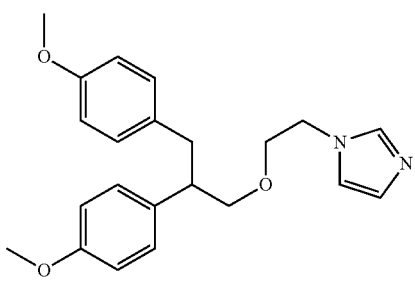 SKF96365<br>1-[2-(4-methoxyphenyl)-2-[3-(4-methoxyphenyl)propoxy]ethyl-1H-imidazol | 12 |
| 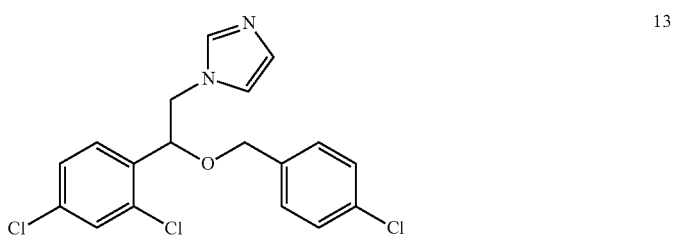 Econazole<br>1-[2-[(4-chlorophenyl)methoxy]-2-(2,4-dichlorophenyl)ethyl]-1H-imidazol | 13 |
| 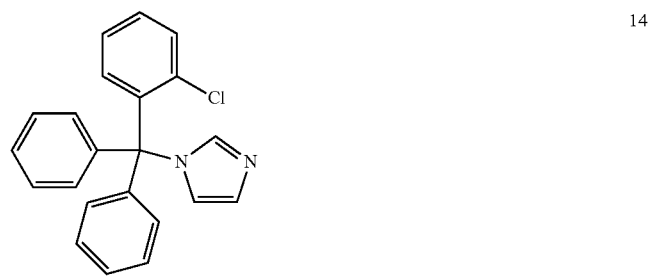 Clotrimazole<br>1-[(2-chlorophenyl)diphenylmethyl]-1H-imidazol | 14 |
| 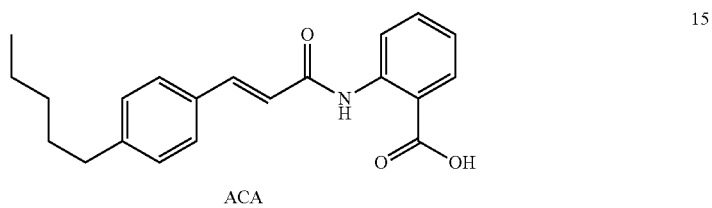 ACA<br>N-(p-amylcinnamoyl)anthranilic acid | 15 |

TABLE 3-continued

| TRPM8 antagonists | |
|---|---|
| Antagonist | Number |
| 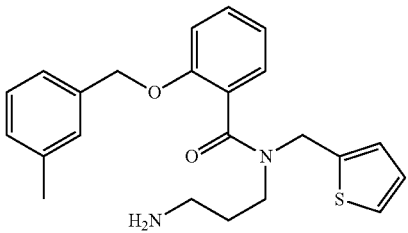<br>AMTB<br>N-(3-aminopropyl)-2-{[(3-methylphenyl) methyl]oxy}-N-(2-thienylmethyl)-benzamide | 16 |
| 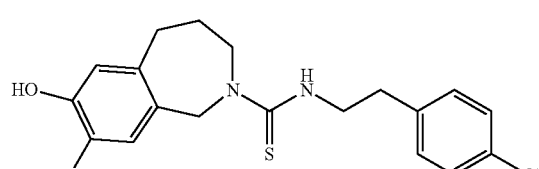<br>Capsazepine<br>N-[2-(4-chlorophenyl)ethyl]-1,3,4,5-tetrahydro-7,8-dihydroxy-2H-2-benzazepine-2-carbothioamide | 17 |
| 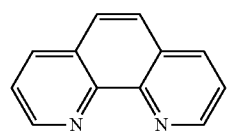<br>Phenanthroline | 18 |
| 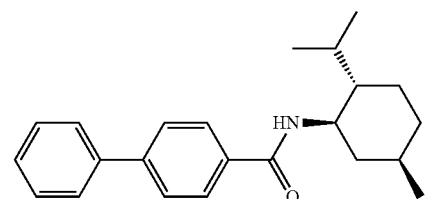<br>MAD1d<br>N-[(1R,2S,5R)-2-Isopropyl-5-methylcyclohexyl]biphenyl-4-carboxamide | 19 |
| 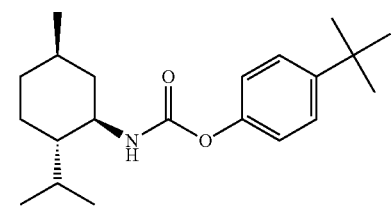<br>MAD2e<br>4-tert-Butylphenyl (1R,2S,5R)-2-isopropyl-5-methylcyclohexylcarbamate | 20 |

TABLE 4

Summary of TRPM8 antagonist Potential inhibitor of different inhibitors of the native TRPM8 channel in cold or at 100 μM of menthol, measured using calcium microscopy (CI), "fluorometric imaging plate reader assay" (FL), spectrofluorimeter (SF) or patch-clamp electrophysiology (EP).

| Compound | $IC_{50}$ cold (μM) | $IC_{50}$ menthol (μM) |
|---|---|---|
| BCTC | $0.68 \pm 0.06^{a\ (CI)}$ | $0.47 \pm 0.01^{b\ (CI)}$ |
|  | $0.54 \pm 0.04^{a\ (EP)}$ | $0.34 \pm 0.04^{b\ (EP)}$ |
|  |  | $0.143 \pm 0.019^{f\ (EP)}$ |
| CTPC | N/A | $0.131 \pm 0.014^{f\ (EP)}$ |
| thio-BCTC | N/A | $3.5 \pm 1.1^{c\ (FL)}$ |
| SB-452533 | N/A | $0.571 \pm 0.077^{f\ (EP)}$ |
| SKF96365 | $1.0 \pm 0.2^{a\ (CI)}$ | $3 \pm 1^{b\ (CI)}$ |
|  | $0.8 \pm 0.1^{a\ (EP)}$ |  |
| Econazole | $0.42 \pm 0.07^{d\ (CI)}$ | N/A |
| Clotrimazole | $8 \pm 1^{d\ (CI)}$ | $1.2^{e\ (EP)}$ |
| ACA | N/A | $3.9^{g\ (FL)}$ |
| AMTB | N/A | $6.23 \pm 0.02^{h\ (FL)}$ |
| Capsazepine | $12 \pm 2^{d\ (CI)}$ | $18 \pm 1^{c\ (FL)}$ |
| Phenanthroline | $100 \pm 20^{a\ (CI)}$ | N/A |
|  | $180 \pm 20^{a\ (EP)}$ |  |
| MAD1d | N/A | $0.02 \pm 0.002^{i(SF)}$ |
| MAD2e | N/A | $0.1 \pm 0.02^{i(SF)}$ |

The data come from:
[a]{Malkia, et al. 2007 J Physiol. 581(Pt 1): 155-74.};
[b]modified by {Madrid, 2006 J Neurosci. 26(48): 12512-25.};
[c]{Behrendt, et al. 2004 Br J Pharmacol. 141(4): 737-45};
[d]{Malkia, et al 2009 Mol Pain. 5: 62.};
[e]{Meseguer, et al. 2008. J Neurosci. 28(3): 576-86.};
[f]{Weil, 2005 Mol Pharmacol. 68(2): 518-27.};
[g]{Kraft, et al. 2006 Br J Pharmacol. 148(3): 264-73},
[h]{Lashinger, et al. 2008 Am J Physiol Renal Physiol. 295(3): F803-10.},
[i]{Ortar, et al. 2010 Bioorg Med Chem Lett. 20(9): 2729-32}. The data from whole cell patch-clamp are expressed as +80 mV$^{a,b}$, +50 mV$^e$, or −70 mV$^f$.
Note:
the results of AMTB were obtained with icilin instead of with menthol. The results for MAD1d and MAD2e were obtained with 20 μM menthol at 22° C.

Antisense Oligonucleotides

In a particular embodiment, an antisense oligonucleotide specific for inhibiting the expression of the gene encoding TRPM8 is used, for instance, inhibiting transcription and/or translation of nucleic acid encoding TRPM8 (of which activity it is intended to inhibit). Antisense oligonucleotides can bind to their potential target by conventional base complementariness or, for instance, in case they bind to bicatenary DNA, through specific interactions in the major sulcus of the double helix. For its use in this invention, a construction comprising an antisense oligonucleotide can be distributed, for instance, as an expression plasmid that, when transcribed in the cell, produces RNA that is complementary at least to a single part of the cell mRNA encoding TRPM8. Alternatively, the antisense construction is a probe of oligonucleotides that is generated ex vivo and that, when placed inside the cell, causes the inhibition of the gene expression hybridising with mRNA and/or genomic sequences of target nucleic acid. These oligonucleotide probes are preferably modified oligonucleotides, that are resistant to endogenous nucleases, for instance, exonucleases and/or endonucleases, and that are therefore stable in vivo. Illustrative nucleic acid molecules for use as antisense oligonucleotides include DNA analogues of phosphoramidate, phosphothionate, and methylphosphonate (see for instance US5176996, US5264564 and US5256775). In addition, for a review of the general approximations to construct useful oligomers in antisense therapy see for instance, Van der Krol et al., BioTechniques 6: 958-976, 1988; and Stein et al., Cancer Res 48: 2659-2668, 1988.

With regard to the antisense oligonucleotide, oligodeoxyribonucleotide regions derived from the site of onset of translation, for instance between −10 and +10 of the target gene, are preferred. The antisense approximations imply the oligonucleotide design (either DNA, either RNA) complementary to the mRNA encoding the target polypeptide. Antisense oligonucleotides will bind to the mRNA transcripts, avoiding translation.

Oligonucleotides complementary to untranslated, uncoded 5' or 3' regions of a gene in an antisense approximation might be also used to inhibit the translation of that mRNA. Oligonucleotides complementary to the untranslated 5' region of mRNA should include the complement of the AUG starting codon. Oligonucleotides complementary to the mRNA coding regions are less effective translation inhibitors, but could be also used according to the invention. If they are designed to hybridise with the 5', 3' or coding region of the mRNA, antisense nucleic acids should have at least 6 nucleotides of length and have preferably less than around 100 and more preferably less than about 50, 25, 17 or 10 nucleotides of length.

Studies in vitro must be performed preferably to measure the ability of antisense oligonucleotides to inhibit gene expression. Advantageously, these studies will use controls that distinguish between antisense gene inhibition and non-specific biological effects of oligonucleotides. It is also preferred that these studies compare the RNA levels or target protein to those of an internal control of RNA or protein. The results obtained using antisense oligonucleotides can be compared to those obtained using a control oligonucleotide. It is preferred that the control oligonucleotide has about the same length as the test oligonucleotide and that the oligonucleotide sequence differs from the antisense sequence no more than necessary to prevent specific hybridization of the target sequence.

Antisense oligonucleotides can be DNA or RNA or chimerical mixtures or derivatives or modified versions thereof, of single chain or double chain. The oligonucleotide can be modified in the base, in the sugar or in the skeleton of phosphate, for instance, to improve the stability of the molecule, its hybridization ability, etc. The olignucleotide can include other bound groups, such as peptides (for instance, to target them to host cell receptors) or agents to help transport through the cell membrane (Letsinger et al., Proc. Natl. Acad. Sci. U.S.A. 86: 6553-6556, 1989; Lemaitre et al., Proc. Natl. Acad. Sci. 84: 648-652, 1987; WO88/09810) or the blood-brain barrier (WO89/10134), interspeding agents (Zon, Pharm. Res. 1988. 5: 539-549). For this purpose, the oligonucleotide can be conjugated with another molecule, for instance, a peptide, a carrier agent, a cut agent triggered by hybridation, etc.

In some cases, it can be difficult to reach the intracellular concentrations of the antisense oligonucleotide sufficient to remove the translation of endogenous mRNAs. Therefore, a preferred approximation uses a construction of recombinant DNA where the antisense oligonucleotide is placed under the control of a strong promoter of pol III or pol II.

Alternatively, the expression of the target gene can be reduced targeting deoxyribonucleotide sequences complementary to the regulatory region of the gene (i.e., the promoter and/or enhancers) to form triple helix structures that prevent transcription of the gene in the target cells in the body (Helene et al, Anticancer Drug Des. 6(6): 569-84, 1991).

In some embodiments, antisense oligonucleotides are antisense morpholins.

DNA Enzymes

In another particular embodiment, a specific DNA enzyme is used to inhibit the expression of the gene encoding TRPM8. The DNA enzymes contain some of the mechanistic characteristics of both the technologies of antisense oligonucleotides and of ribozyme technologies. The DNA enzymes are designed so that they recognise a target sequence of the particular nucleic acid sequence (in this case, the sequence encoding TRPM8), similar to the antisense oligonucleotide; however, similarly to ribozyme, they are catalytic and cut specifically the target nucleic acid.

Ribozymes

In another particular embodiment, a specific ribozyme is used, that is designed to cut catalytically transcripts of a target mRNA to prevent translation of the mRNAs encoding TRPM8 of which activity it is intended to inhibit. Ribozymes are RNA enzyme molecules that can catalyse the specific RNA cut [for a review see Rossi, 1994. Current Biology 4: 469-471]. The sequence of ribozyme molecules preferably includes one or more sequences complementary to the target mRNA and the well-known sequence responsible for the mRNA cut or a functionally equivalent sequence [see for instance, US5093246].

The ribozymes used in the present invention include hammerhead ribozymes, endoribonuclease RNAs, etc. [Zaug et al., 1984. Science 224:574-578].

Ribozymes can be made up of modified oligonucleotides (for instance, to enhance stability, directioning, etc.) and should be distributed to cells expressing the target gene in vivo. A preferred distribution method involves using a DNA construction that "codes" the ribozyme under the control of a strong constitutive promoter of pol III or pol II, so that the transfected cells will produce sufficient amounts of the ribozyme for destroying the endogenous target messengers and inhibit translation. As ribozymes, contrary to other antisense molecules, are catalytic, they require a lower intracellular concentration to be effective.

MicroRNAs

In another particular embodiment, a microRNA specific for the sequence encoding TRPM8 is used. As known, a microRNA (miRNA) is a single-stranded RNA, of a length between 21 and 25 nucleotides, that has the ability to regulate the expression of other genes by several processes, using for this the RNA interference route.

iRNA

In another particular embodiment, interference RNA (iRNA) is used, such as a small interference RNA (siRNA) specific for the sequence that codes TRPM8 which activity it is intended to inhibit.

Small interference RNAs or siRNA are agents able to inhibit the expression of a target gene by RNA interference. A siRNA can be synthesised chemically or, alternatively, it can be obtained by transcription in vitro or can be synthesized in vivo in the target cell. siRNAs typically consist of a double-chain of RNA of between 15 and 40 nucleotides in length, that may contain a protuberant 3' and/or 5' region of 1 to 6 nucleotides. The length of the protuberant region is independent of the total length of the siRNA molecule. siRNAs act by degradation or silencing post-transcription of the target messenger.

siRNAs can be the so-called shRNA (short hairpin RNA), characterised in that antiparallel chains forming the siRNAs are connected by a loop or hairpin region. shRNAs can be coded by plasmids or virus, particularly retrovirus, and under the control of promoters such as the promoter U6 of the RNA polymerase III.

In a particular embodiment, siRNAs that can be used in this invention are substantially homologue to the mRNA of the gene encoding RTPM8 or the genome sequence encoding this protein. "Substantially homologous" are defined as those with a sequence which is sufficiently complementary or similar to the target mRNA, so that the siRNA can cause degradation thereof by RNA interference. The siRNAs adequate to cause this interference include siRNAs formed by RNA, as well as siRNAs containing different chemical modifications, such as:

siRNAs where the bonds between nucleotides are different to those occurring in nature, such as phosphorothioate bonds;

conjugates of the RNA chain with a functional reagent, such as a fluorophore;

modifications in the ends of the RNA chains, in particular end 3' by modification with different functional groups of hydroxyl in position 2';

nucleotides with modified sugars, such as O-alkylated rests in position 2', such as 2'-O-methylribose or 2'-O-fluorosibose;

nucleotides with modified bases, such as halogen bases (for instance, 5-bromouracyl and 5-iodouracyl), alkylated bases (for instance, 7-methylguanosin).

siRNAs and shRNAs that can be used in this invention can be obtained using a number of techniques known by a person skilled in the art. The region of the nucleotide sequence encoding TRPM8 taken as the basis to design siRNAs is not limiting and can contain a region of the coding sequence (between the initiation codon and the ending codon) or, alternatively, can contain sequences of the untranslated 5' or 3' region, preferably between 25 and 50 nucleotides of length and in any position in position sense 3' from the initiation codon. A method for designing a siRNA involves the identification of motifs AA(N19)TT, where N can be any nucleotide in the sequence encoding TRPM8, and the selection of those with a high content in G/C. If this motif is not found, motif NA(N21) can be identified, where N can be any nucleotide.

In a particular embodiment, the TRPM8 inhibitor is an iRNA specific for TRPM8, such as a specific iRNA selected from the group formed by the specific iRNAs shown in Table 3 (5) [SEQ ID NO: 3, SEQ ID NO: 4, SEQ ID NO: 5, SEQ ID NO: 6, SEQ ID NO: 7, SEQ ID NO: 8, SEQ ID NO: 9].

Inhibitory Peptides

In another particular embodiment, a TRPM8 inhibitor peptide is used to prevent that this protein fulfils any of its functions, in particular, the crossing of sodium and calcium ions through the channel.

The term "inhibitor peptide", as used here, makes reference to peptides that can bind to TRPM8 and inhibit its activity as explained above, i.e., prevent that sodium and calcium ions cross the TRPM8 channel.

Inhibitory Antibodies

In another particular embodiment, a TRPM8 inhibitor antibody is used to prevent that this protein fulfils any of its functions, in particular, the crossing of sodium and calcium ions through the channel. Therefore, a TRPM8 "inhibitor" antibody, as used here, relates to an antibody that can bind to TRPM8 specifically and inhibit the passage of sodium and calcium ions through the channel. The antibodies can be prepared using any of the methods known by a person skilled in the art. Once antibodies with ability to bind to TRPM8 are identified, those able to inhibit the activity of this protein will be selected using an assay for identification of inhibitory agents [see, for instance, Metz; S. et al. 2008. J. Biol. Chem. 283:5985-5995].

Chemical Compounds

In another particular embodiment, a chemical compound that reduces the activity of TRPM8 when contacting this protein is used. Illustrative examples, not limiting these chemical compounds, include the compounds mentioned in Table 3 (8 to 20) and include BCTC, CTPC, thio-BCTC, SB-452533, SKF96365, Econazole, Clotrimazole, ACA, AMTB, Capsazepine, Phenanthroline, MAD1d and MAD2e.

In a particular embodiment, the TRPM8 antagonist used in the second use of the invention is an antagonist selected from: antisense antinucleotide specific for the sequence of the gene encoding TRPM8, DNA enzyme specific for the TRPM8 sequence, microRNA specific for the gen encoding TRPM8, ribozyme specific for the sequence of the gene encoding TRPM-8, interference RNA specific for the sequence of the gene encoding TRPM8, peptide with ability to bind specifically to TRPM8 and inhibit its activity, antibody with activity to bind specifically to TRPM8 and inhibit the activity of this channel, BCTC (N-(4-tert-butyl-phenyl)-4-(3-chloropyridin-2-yl)tetrahydropyrazine-1(2H)-carboxamide), CTPC ((2R)-4-(3-chloro-2-pyridinyl)-2-methyl-N-[4-(trifluoromethyl) phenyl]-1-pyperazine-carboxamide), thio-BCTC (N-(4-tert-buthyl-phenyl)-4-(3-chloropyridin-2-yl) tetrahydropirazine-1 (2H)-(thio) carboxamide), SB-452533 (N-(2-bromophenyl)-N'-(2-[ethyl(3-methylphenyl)amino] ethyl)urea), SKF96365 (1-[2-(4-methoxyphenyl)-2-[3-(4-methoxyphenyl)propoxy]ethyl-1H-imidazol), Econazol (1-[2-[(4-chorophenyl)methoxy]-2-(2,4-dichlorophenyl)ethyl]-1H-imidazol), Clotrimazol (1-[(2-chlorophenyl) diphenylmethyl]-1H-imidazol), ACA (N-(p-amylcinnamoyl) anthranilic acid), AMTB (N-(3-aminopropyl)-2-{[(3-methylphenyl)methyl]oxy}-N-(2-thienylmethyl)-benzamide), Capsazepine (N-[2-(4-chlorophenyl)ethyl]-1,3,4,5-tetrahydro-7,8-dihydroxy-2H-2-benzazepine-2-carbothioamide), Phenantrolin, MAD1d (N-[(1R,2S,5R)-2-Isopropyl-5-methylcyclohexyl]biphenyl-4-carboxamide), MAD2e (4-tert-Butylphenyl(1R,2S,5R)-2-isopropyl-5-methylcyclohexylcarbamate).

In another particular embodiment, the TRPM8 antagonist is a specific antagonist for TRPM8.

Second Composition of the Invention

In another aspect, the invention relates to a composition (hereinafter second composition of the invention) comprising at least one TRPM8 antagonist and at least one drug useful for the treatment of epiphora, and, if desired, a pharmaceutically acceptable vehicle.

The term "TRPM8 antagonist" has been described previously and is used in the same manner in relation to the second composition of the invention.

The term "pharmaceutically acceptable vehicle" as well as the administration routes of the composition have been previously described in the context of the first composition of the invention.

The word "epiphora" has been described in detail previously and is used in the same manner in the context of this composition indicating, therefore, the epiphora occurring as a symptom in different disorders, such as Graves-Basedow disease, ulcers in the cornea, Ackerman syndrome, allergies (animals, pollen etc), bacterial conjunctivitis, blepharitis, facial nerve palsy, ectropion or obstruction in the nasolacrimal duct or the lacrimal sac.

In a particular embodiment, the TRPM8 antagonist used in the second composition of the invention is an antagonist selected from: antisense antinucleotide specific for the sequence of the gene encoding TRPM8, DNA enzyme specific for the TRPM8 sequence, microRNA specific for the gene encoding TRPM8, ribozyme specific for the sequence of the gene encoding TRPM-8, interference RNA specific for the sequence of the gene encoding TRPM8, peptide with ability to bind specifically to TRPM8 and inhibit its activity, antibody with activity to bind specifically to TRPM8 and inhibit the activity of this channel, BCTC (N-(4-tert-butyl-phenyl)-4-(3-chloropyridin-2-yl)tetrahydropyrazine-1 (2H)-carboxamide), CTPC ((2R)-4-(3-chloro-2-pyridinyl)-2-methyl-N-[4-(trifluoromethyl)phenyl]-1-pyperazine-carboxamide), thio-BCTC (N-(4-tert-buthyl-phenyl)-4-(3-chloropyridin-2-yl)tetrahydropirazine-1 (2H)-(thio) carboxamide), SB-452533 (N-(2-bromophenyl)-N-(2-[ethyl (3-methylphenyl)amino]ethyl)urea), SKF96365 (1-[2-(4-methoxyphenyl)-2-[3-(4-methoxyphenyl)propoxy]ethyl-1H-imidazol), Econazole (1-[2-[(4-chorophenyl)methoxy]-2-(2,4-dichlorophenyl)ethyl]-1H-imidazol), Clotrimazole (1-[(2-chlorophenyl)diphenylmethyl]-1H-imidazol), ACA (N-(p-amylcinnamoyl)anthranilic acid), AMTB (N-(3-aminopropyl)-2-{[(3-methylphenyl)methyl]oxy}-N-(2-thienyl-methyl)-benzamide), Capsazepine (N-[2-(4-chlorophenyl) ethyl]-1,3,4,5-tetrahydro-7,8-dihydroxy-2H-2-benzazepine-2-carbothioamide), Phenanthroline, MAD1d (N-[(1R,2S, 5R)-2-Isopropyl-5-methylcyclohexyl]biphenyl-4-carboxamide), MAD2e (4-tert-Butylphenyl(1R,2S,5R)-2-isopropyl-5-methylcyclohexylcarbamate).

The drugs useful for the treatment of epiphora are known by a person skilled in the art, such as antibiotics, as well as the compositions described in documents CN101612199A, WO08066644, RU2305517C, CN1775261A, CN1775263A, CN1565501A, CN1199617A, and JP57179121A.

In another aspect, the invention relates to the use of a second composition according to the invention for manufacturing a medicament for the treatment of epiphora. In another aspect, the invention relates to a second composition according to the invention for use in the treatment of epiphora. In a third aspect, the invention relates to a method for the treatment of epiphora in a subject comprising the administration to this subject of a second composition of the invention.

The following example illustrates the invention and must be considered limiting of its scope.

EXAMPLE

To define functionally the thermal sensitivity and encoding capacity of intact cold-sensitive nerve terminals, nerve terminal impulse (NTI) activity from the cornea of wild-type mice eyes was recorded 'in vitro' (Brock, J. A., et al., 1998. J. Physiol 512:211-217). Cold thermoreceptor endings were identified by their spontaneous nerve impulse at 34° C. that increased in frequency with cooling, was silenced by rewarming as well as their response to the application of menthol (FIG. 1A) (Schafer, K., et al., 1986. J. Gen. Physiol 88:757-776). 72% of cold-sensitive endings also responded to heat pulses (paradoxical response) (Long, R. R. 1977. J. Neurophysiol. 40:489-502) (FIG. 1A) and to 100 nM capsaicin (65%).

The spontaneous trigger frequency of cold-sensitive nerve terminals at the basal temperature (34° C.) was 4.0±0.4 impulses/s (n=55). Cold-sensitive nerve terminals fried spontaneously response either many unique potential as, occasionally, in bursts of two or more action potentials at quite regular intervals. Cooling pulses from 34° C. to 20° C. evoked a impulses discharge increasing progressively with the temperature reduction, reaching a peak frequency and slowed down or silenced later, upon reaching the lower temperatures values (FIGS. 1A and 1B). The time course of mean trigger frequency and temperature decrease during cooling ramps registered for a total of 55 cold-sensitive endings is represented in FIG. 1B. Temperature thresholds to evoke frequency increases with cooling ramps were smaller than 2° C. (mean value −1.5±0.2° C., FIG. 1C). About 30% of the term-sensitive units already increased significantly their trigger frequency when temperature had decreased 1° C. or less. The mean value of peak frequency during cooling ramp was 37.6±1.8 impulses/s (n=55).

Thermal sensitivity of corneal cold thermoreceptors, expressed as the change in trigger frequency per degree Celsius of temperature decrease during continuous cooling ramps varied among registered units. The mean slope was 6.3±1.0 impulses/s/° C. (n=55) (red line FIG. 1D). The capacity of cold-sensitive endings to encode sustained temperature values applying cooling steps of −2.5° C., between 34° C. and 24° C. were also evaluated (FIG. 1E). The initial temperature drop produced a transient increment in trigger frequency that adapted to a new steady level. Corneal cold thermoreceptors were able to code static temperature over a wide temperature range. The response to low temperature was characterized by an increase in the trigger frequency; a marked change in the firing pattern which became bursting in many cases (FIG. 1E; Table 1), and transient modifications of the shape of the potentials recorded (Brock, J. A., et al., 1998. J. Physiol 512:211-217. FIG. 1F summarizes static and dynamic changes in trigger frequency for 10 cold thermoreceptors and it shows the remarkable thermal sensitivity of corneal receptors to small changes in temperature.

Menthol (50 µM), a well-known activator of cold-sensitive afferents (Schafer, K., et al., 1986, J. Gen. Physiol. 88:757-776), increased spontaneous activity in 98% of the tested endings (FIG. 1A) (from 3.4±0.3 impulses/s to 18.4±1.4 impulses/s; p<0.001, n=44, paired t-test). The percentage of terminals that had a bursting firing pattern at 34° C. was almost ten times higher during perfusion with menthol (44%) than before treatment (5%). Menthol sensitized the response of endings to cooling: in the presence of menthol, cooling ramps evoked an augmented trigger frequency, reaching peak frequency at higher temperatures (control: 26.7±0.5° C.; menthol: 28.6±0.5° C., n=44; p<0.001 paired t-test) and silencing itself at higher temperatures (control: 23.8±0.4° C.; menthol: 25.2±0.4° C.; p<0.05, paired t-test). BCTC is a strong and reversible blocker of TRPM8 ion channels in vitro Madrid, R. et al. 2006. J. Neurosci. 26:12512-12525, Jordt, S. E. et al. 2004. Nature 427:260-265). Effect of a saturating concentration of BCTC (10 µM) on sensitive endings was studied. Spontaneous activity and increase of trigger frequency of cold- and menthol-evoked discharges decreased gradually and almost silenced after BCTC perfusion during 90 min. These effects of BCTC were also observed in TRPA1 (−/−) mice. The decline in activity was reversed partially upon BCTC removal and was not observed in the absence of the drug, suggesting that the activity of thermo sensitive nerve endings was largely dependent on TRPM8 channels. In contrast to the stimulating effect of menthol, the specific TRPA1 agonist allyl-isothiocyanate (AITC, 100 µM) (Bandell, M. et al. 2004; Neuron 41:849-857), tested in 28 cold-sensitive nerve endings failed to modify the spontaneous or cold-evoked activity in 24 of them. Only four nerve endings showed a significant increase in the trigger frequency when perfused with AITC at basal temperature (data not shown), suggesting that expression of TRPA1 channels is absent or minor in the majority of cold-sensitive corneal endings. Altogether, these results are also consistent with a limited overlap of TRPM8 and TRPA1 expression noted previously (Story, G. M. et al. 2003. Cell 112:819-829).

IKD is a shaker-like, voltage-gated potassium current that acts as an excitability brake against the activation of sensory neurons by temperature decreases, contributing to determine the thermal threshold in thermoreceptors (Madrid, R., et al. 2009. J. Neurosci. 29:3120-3131). Current IKD blocker 4-aminopyridine (4-AP, 100 µM) was used to explore whether this current affected the thermal sensitivity of corneal cold nerve endings. In three out of nine studied units, spontaneous activity increased significantly after perfusion with of 4-AP, but no parallel changes in the cold threshold of these endings was noticed. Contrarily, in all terminals treated with 4-AP, the mean peak frequency of cold responses was depressed 39±6% of the control value (p<0.001, n=9). Altogether, these data suggest that the thermal threshold of cold receptor nerve endings of the mouse cornea is not determined, at least significantly, by shaker-like Kv1 channels and that these endings belong to the low-threshold type of cold receptor neurons (Belmonte, C., et al. 2009. Exp Brain Res. 196: 13-30).

Figure 2:
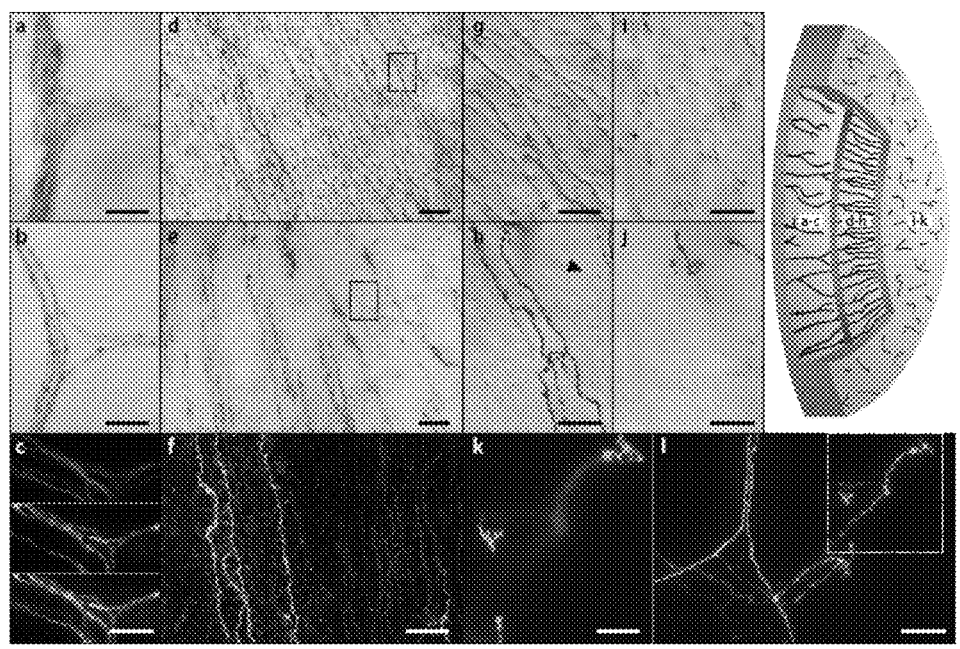
FIG. 2. Whole-mount immunohistochemistry of corneal sensory nerve fibers of TRPM8-EYFP mouse. a, b and c are examples of stromal nerve bundles entering the peripheral cornea to form the stromal plexus. In a, all sensory nerve fibers contained in the nerve bundle were stained with an antibody against neuron-specific class III beta tubulin (Tuj-1), while in b only nerve fibers reacting to an antibody against the green fluorescent protein (GFP) were stained. c shows a double immunofluorescence staining of stromal nerves with Tuj-1 (upper panel) and with a GFP antibody (middle panel) and the corresponding merged image (lower panel), to evidence the reduced proportion of presumed cold-sensitive fibers among the general population of sensory nerve fibers. d, e and f show the characteristic architecture of nerve fibers running in the basal epithelium layers of the cornea (subbasal plexus), where they appear as straight and roughly parallel beaded fibers (leashes), that run for long distances from the periphery towards the center of the cornea. In d, all subbasal sensory fibers (Tuj-1 positive) were stained, while in e, only those immunoreactive to GFP are seen. F shows a double immunofluorescence of Tuj-1 positive (grey) and GFPpositive fibers (white) to illustrate the paucity of presumed TRPM8-positive axons. G and h depict a higher magnification view of the areas dashed in d and e respectively, to evidence in more detail the morphology of the beaded fibers and their branches that ascend perpendicularly from the basal layers of the corneal epithelium towards the outermost superficial layers, giving sometimes end terminals at this level (arrowhead). In i and j, the same areas depicted in g and h are shown in a more superficial plane of focus to illustrate the appearance of superficial epithelial nerve terminals: of all corneal sensory nerve fibers (i) and of GFP-positive, putative cold-sensitive terminals (j). The different morphology and reduced branching of presumed TRPM8-positive terminals is also illustrated in k using upright fluorescence microscopy. l presents a Z-stack compiled in single image that illustrates the trajectory of the axons running from the stroma to the corneal surface that finally gives rise to the pencillate-like GFP-positive endings (dashed square) shown in k. Upper right corner: drawing of the mouse cornea that illustrates schematically the location of the various types of nerves shown in the different panels of the figure. a-c corresponds to the anterior third of the stroma, where stromal nerves are found, d-h represents the leashes in the basal epithelium layer and i-k the corneal surface with the nerve terminals. Scale bars: a-c is 70 μm; d and e is 150 μm; f-l is 40 μm.

Subsequently, the presence, morphology and density of nerve fibers presumably expressing the cold-sensitive channel TRPM8 was analyzed in the mouse cornea, using mice engineered to express the enhanced yellow fluorescent protein (EYFP) under the control of trpm8 regulatory sequences (TRPM8-EYFP mice, FIG. 2). Presumed TRPM8-positive nerve fibers were distributed homogeneously throughout the entire cornea. Stromal nerve bundles run into the external third of the corneal stroma (FIG. 2A-C). Approximately one out of nine stromal axons was TRPM8-positive (FIG. 2C). Once branches from the stromal nerve plexus penetrate the Bowman's layer located between stroma and corneal epithelium, they ramify below basal epithelium cells into several subbasal nerve fibers (leashes) that run parallel from each other towards the center of the cornea (FIG. 2D-H). Some TRPM8-positive subbasal fibers gave rise to single end terminals already within this subbasal plexus (FIG. 2H, arrowhead). However, most of them give collaterals that ascend towards the superficial epithelial layers, ending as asymmetrical radiated clusters (FIG. 2 I-K). Unlike non-fluorescent sensory fibers, presumably polymodal and mechanonociceptive fibers, TRPM8-positive terminal axons branched sparsely within the epithelium to end as a reduced number of pencillated terminals in the outermost superficial epithelial cell layers (FIG. 2J-L). The subbasal epithelial leashes and the intraepithelial end terminals showed in all cases a beaded-like morphology (FIG. 2H-K). By using double immunofluorescence staining against green fluorescence protein (GFP) and against neurofilaments, it was determined that putative cold receptor fibers represented around 12% of the total number of subbasal nerve fibers and about 10% of the superficial intraepithelial nerve terminals (see also the Methods section; FIG. 2C, F, K, L).

Figure 3:
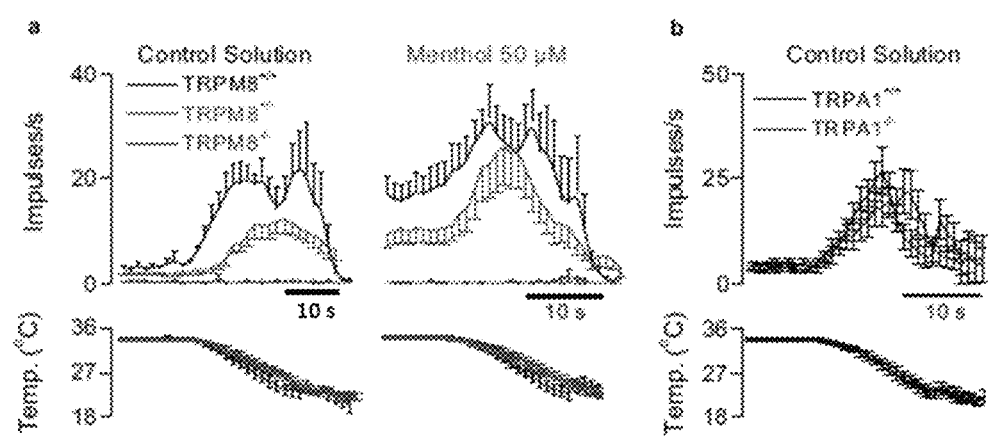
FIG. 3. Response to cooling ramps of corneal terminals from TRPM8 (−/−), TRPM8 (+/−) and TRPA1(−/−) mice and wild type mice. a. Mean trigger frequency rate (impulses/s) (upper panel) during a cooling ramp (lower panel) recorded in 143 nerve terminals from TRPM8(−/−) mice (thin trace), in 11 terminals from TRPM8 (+/−) mice (discontinuous trace) and 12 terminals from wild type litter mates (continuous trace), in control solution (left) and in the presence of 50 μM menthol (right). b Mean trigger frequency rate of 11 terminals from TRPA1(−/−) mice (thin trace) and 13 terminals from wild type litter mates (thick trace) during a cooling ramp. Data are mean±SEM.

Next, the contribution of TRPM8 channels to cold sensitivity was determined, exploring cold-evoked nerve impulses discharge in TRPM8(−/−)-EGFP ki-mice (Dhaka, A. et al. 2007. Neuron 54:371-378). An attempt was record sensory endings responses in 12 TRPM8(−/−) corneas. However, spontaneous activity was detected in only 14 nerve endings, out of hundreds of trials in which the complete corneal surface was repeatedly explored with the recording pipette (FIG. 3A, dotted trace). In these cases, spontaneous activity was of low frequency (0.6±0.2 impulses/s, n=14) and only in one of the TRPM8(−/−) terminals, the trigger frequency increased during a cooling ramp, with a threshold temperature of 28.4° C.; and a peak frequency during the ramp of 3 impulses/s at 24.7° C. Menthol is a potent activator of TRPM8 channels (McKemy, D. D., et al. 2002. Nature 416:52-58). 50 µM menthol perfusion produced no increase in the trigger frequency or at basal temperature of 34° C. or during cooling ramps (n=6) (FIG. 3A, punctuated trace). This result is consistent with the existence of dependence of spontaneous activity and cold-evoked activity in cold-sensitive terminals on the expression of TRPM8. Capsaicin (100 nM), tested in six of the active units registered in TRPM8(−/−) corneas, evoked a few impulses in two endings (5 and 8 impulses, respectively) and a vigorous, discharge lasting more than 30 s in another.

In contrast with the profound inhibition of spontaneous activity and cold-evoked activity observed in TRPM8(−/−) mice, corneal nerve endings of TRPA1(−/−) mice (Kwan, K. Y. et al. 2006. Neuron, 50:277-289) showed a trigger frequency values and responses to cooling similar to that of wild type animals (FIG. 3B). Altogether, these results confirm that TRPA1 channels are not critical molecular determinants for cold sensitivity of corneal cold-sensitive endings. These results are consistent with our previous findings obtained in cultured trigeminal sensory neurons (J. Neurosci., 2009, 29:3120-3131). To exclude the possibility that cold nerve terminals in the cornea of TRPM8(−/−) were absent or morphologically altered, these corneas were stained with antibodies against GFP to visualize the morphology of the nerve fibers that expressed the truncated TRPM8 channel (Dhaka, A., et al. 2008. J. Neurosci. 28:566-575). The distribution of stained nerve fibers in different regions of the corneal circumference was more variable among TRPM8(−/−) animals. Nevertheless, the general morphology of epithelial leashes and clustered intraepithelial nerve endings was in all cases similar to that of TRPM8-EYFP positive fibers. Moreover, no significant differences in the overall density of endings was noticed, thus excluding the possibility that the absence of activity and cold response observed in electrophysiology experiments were due to endings not reached by the recording pipette.

Additionally, cold-evoked activity was explored in TRPM8(+/−) mice, in which responsiveness to cold is expected to be reduced by a lower expression of TRPM8.30 channels. In these animals, 30% of the nerve endings were spontaneously active but lacked cold and menthol sensitivity in contrast with wild-type animals, where cold-insensitive units displaying spontaneous activity were exceptional (7%). Among the active nerve endings, the mean spontaneous activity at 34° C. was significantly lower than in TRPM8(+/+) animals (2.2±0.4 impulses/s, vs. 4.4±0.9 impulses/s, n=11; p=0.025, Mann-Whitney test) while during cooling ramps, threshold temperature which is the temperature required to evoke a trigger frequency increase, was established in lower temperature values (30.6±0.5° C. vs. 32.7±0.4° C. p=0.004 Mann-Whitney test), and mean peak frequency during cooling was significantly lower in TRPM8(+/−) corneas than in wild type mice (19.4±3.4 impulse/s vs. 33.8±3.5 impulses/s, p=0.008, t-test) (FIG. 3A, continuous trace). Menthol (50 µM) enhanced trigger frequency in basal temperature, cold threshold and peak frequency in TRPM8(+/−) mice, albeit significantly less than in TRPM8(+/+) animals (FIG. 3A, continuous trace).

Figure 4:
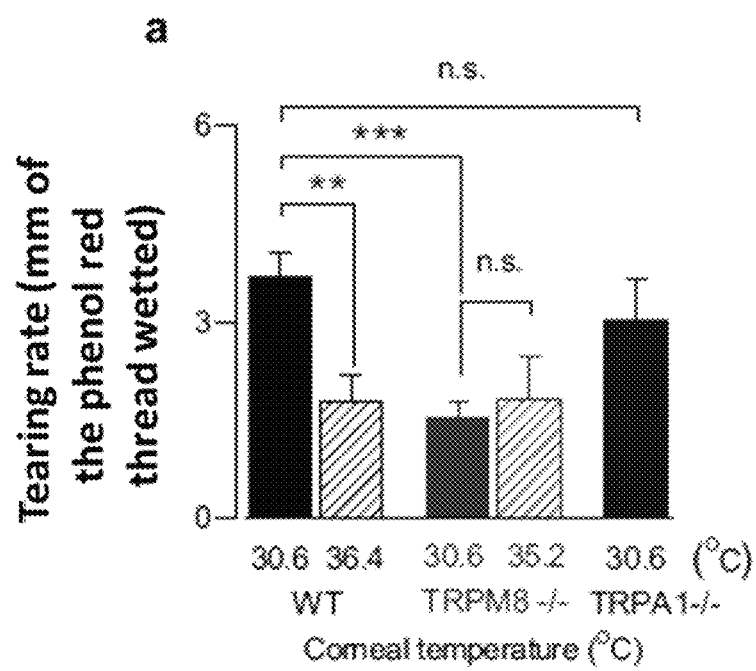
FIG. 4. Dependence of tear secretion rate on corneal temperature. a. Basal tearing rate, expressed as the mean length of the phenol red thread wetted during 2 min, measured in the eyes of anesthetized mice exposed to environmental temperatures of 24.8±0.9° C. and 42.5±0.4° C., under environmental humidity of 63.7±0.4% and 38.2±1.4%, respectively that modified their corneal surface temperature to the values indicated. Shaded and filled columns represent tearing rate in animals at mean neutral (28.4° C.) or hot temperature (42.5° C.), respectively. The number of measures of successive columns is 35, 11, 23, 9 and 6 observations p<0.01, *p<0.001 Mann-Whitney test). b. Increase in tearing rate measured in wild type animals (black columns) and TRPM8−/− (grey columns) elicited by application during 60 s, of a filter paper soaked in capsaicin 1 μM (n=12 and 15) or 500 μM allyl-isothyocyanate. The first column shows the response to the application of vehicle (0.5% DMSO in saline) in wild type animals (n=6). Measurements of tear secretion were performed 1 minute after removing the paper with the drug. Statistically significant differences were found with respect to baseline lacrimation, using the Wilcoxon test (*p<0.05, *p<0.001). c. Mean tearing rate expressed as the wetted length value of the phenol red thread, measured in the eyes of 11 human volunteers at environment temperatures of 18° C., 25° C. and 43° C. that lead to corneal surface temperatures of 32.4±0.4° C.; 34.2±0.1° C. and 36.0±0.2° C. respectively. ANOVA on repeated measures showed significant differences (p<0.01).
Figure 4:
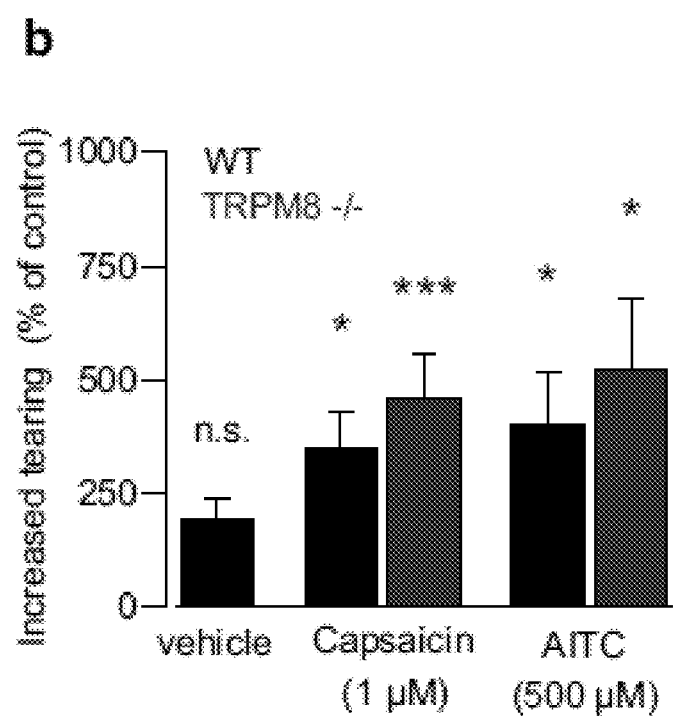
Figure 4:
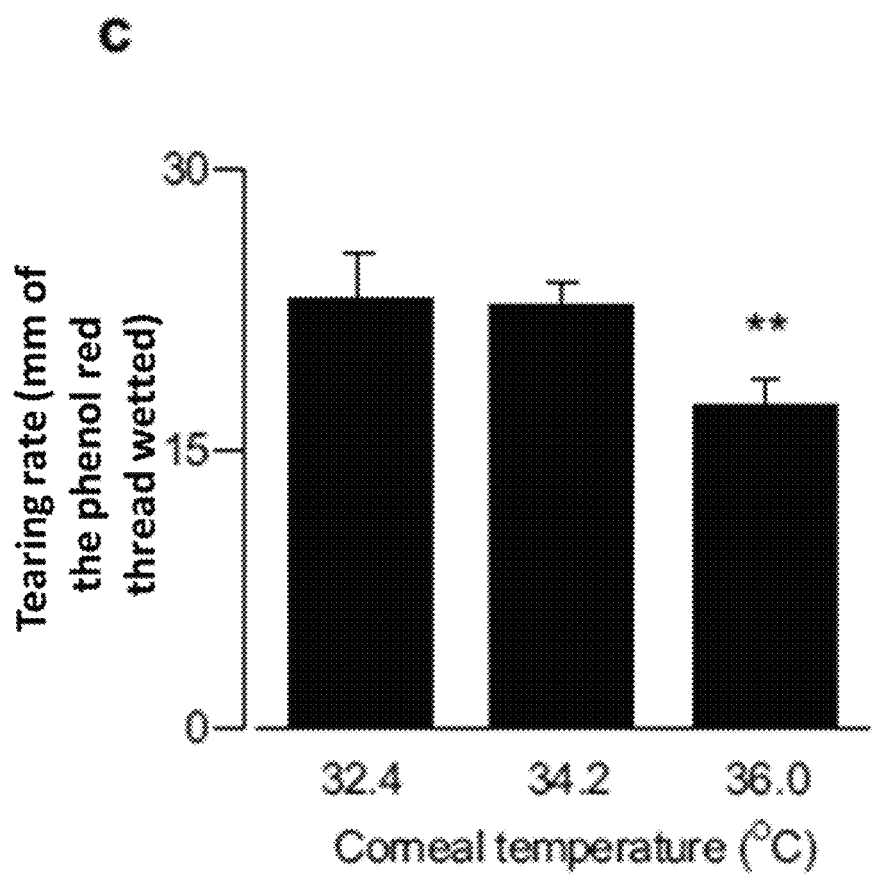

Next, it was reasoned that if tear production is associated to the neural activity of cold thermoreceptor fibers, basal tear flow should be reduced in TRPM8(−/−) mice, in which spontaneous activity is absent. FIG. 4A shows that this was indeed the case. Tear fluid volume, expressed as stained length of phenol thread, which changes color when wetted with tears, collected during 2 min period, measured in TRPM8(−/−) mice under basal conditions (1.5±0.2 mm, n=23) was significantly lower compared to wild-type animals (3.7±0.4 mm, n=35, p<0.001). In contrast, basal tearing rate in TRPA1(−/−) mice was not significantly different from wild-type animals (FIG. 4A, black columns). On another hand, topical application of capsaicin (1 µM) and AITC (500 µM), two well-known stimulating agents of TRPV1 and TRPA1 channels in polymodal nociceptors, but not the vehicle, significantly increased tear flow in the eyes of TRPM8(−/−) and wild type mice (FIG. 4B).

Next, it was tried to confirm whether the relationship between corneal temperature and basal tearing rate was also present in human subjects and measured tearing rate in 11 young human (28.9±1.8 years old) volunteers exposed during 10 minutes to environmental temperatures of 18° C., 25° C. and 43° C. under a constant humidity of 31%, in separate sessions. Exposure to these environmental temperatures drove corneal temperature to 32.4±0.4° C., 34.2±0.1° C. and 36.0±0.2° C., respectively. These values were significantly different (p<0.001, Anova repeated measures). In contrast, only in the 43° C. environment was the tearing rate significantly reduced: 17.1±1.4 mm vs. 22.8±1.2 mm at 25° C. or 23.2±2 3 mm at 18° C. (Anova repeated measures, p=0.006) (FIG. 4C). When exposure to 43° C. (corneal temperature 36±0.1) was repeated with an environmental humidity level of 62.5% reduction of tearing flow was the same (17.6±2.4 mm) than in a 31% humidity environment. These experiments were mimicked in anesthetized wild type and TRPM8(−/−) mice by placing them in the same environmental conditions used in the experiments in humans, that is to say, exposing them to high and neutral environmental temperatures under constant humidity values. When the mean corneal temperature of wild type mice was raised to 36.4±0.2° C. (n=11), tearing decreased to 1.8±0.4 mm (FIG. 4A) while in a neutral environment the mean corneal temperature was 27.2±0.1° C., (n=6) and tearing value was 4.6±0.8 mm (p=0.017 Mann-Whitney test). In contrast, in TRPM8(−/−) mice exposed to similar conditions, tearing flow rate did not differ significantly when the corneal surface temperature varied (FIG. 4A).

The invention claimed is:

1. An ophthalmic composition comprising a therapeutically effective amount of WS-12 (2-isopropyl-5-methyl-cyclohexanecarboxylic acid (4-methoxy phenyl)-amide), wherein the amount of WS-12 can effectively treat or reduce the likelihood of xerophthalmia in a subject in need thereof, and wherein the amount of WS-12 is not cytotoxic.

2. The ophthalmic composition of claim 1, wherein WS-12 acts as a Transient receptor potential cation channel subfamily M member 8 (TRPM8) agonist that has an efficacy of at least 50, 100, 1000 or 2000 times more than the other channel of other members of the Transient receptor potential cation channel subfamily M.

3. The ophthalmic composition of claim 1, wherein the amount of WS-12 per dose ranges from 0.0005 milligrams to 0.1 milligrams.

4. The ophthalmic composition of claim 1, wherein the amount of WS-12 per dose is about 0.0005 milligrams.

5. The ophthalmic composition of claim 1, wherein the amount of WS-12 per dose ranges from 0.007 micrograms/kilogram to 0.01 milligrams/kilogram of body weight.

6. The ophthalmic composition of claim 1, wherein the amount of WS-12 per dose is about 0.007 micrograms/kilogram of body weight.

7. The ophthalmic composition of claim 1, wherein the composition can be administered a variable number of times a day.

8. The ophthalmic composition of claim 1, wherein the composition can be administered from 1 to 4 times a day.

9. The ophthalmic composition according to claim 1, wherein the composition comprises an additional TRPM8 agonist.

10. The ophthalmic composition according to claim 9, wherein the additional TRPM8 agonist is selected from the group consisting of WS-3, WS-5, WS-11, WS-14, WS-23, WS-30, WS-148, menthol, and a combination thereof.

11. The ophthalmic composition according to claim 1, wherein the composition further comprises a drug useful for the treatment of xerophthalmia.

12. The ophthalmic composition according to claim 11, wherein the drug useful for the treatment of xerophthalmia is selected from the group consisting of a corticoid, vitamin A, pylocarpine, hypromellone, carbomer, cyclosporine, and a combination thereof.

13. The ophthalmic composition according to claim 1, wherein the composition comprises a lubricant.

14. The ophthalmic composition according to claim 13, wherein the lubricant is selected from the group consisting of glycerol, hydroxypropyl methylcellulose, hydroxymethyl cellulose, carboxymethyl cellulose, polyethylene glycol, polyvinyl alcohol, hyaluronic acid, castor oil, mineral oil, and combinations thereof.

15. The ophthalmic composition according to claim 1, wherein the composition comprises a pharmaceutically acceptable vehicle.

16. The ophthalmic composition according to claim 1, wherein the subject is an animal subject.

17. A method to treat or reduce the likelihood of xerophthalmia, comprising the administration of a therapeutically effective amount of a composition comprising WS-12 (2-isopropyl-5-methyl-cyclohexanecarboxylic acid (4-methoxyphenyl)-amide) to an individual suffering from xerophthalmia.

18. The method of claim 17, wherein WS-12 acts as a TRPM8 agonist that has an efficacy of 50, 100, 1000 or 2000 times more than the other channel of other members of the Transient receptor potential cation channel subfamily M.

19. The method of claim 17, wherein the dose of WS-12 ranges from 0.0005 milligrams to 0.1 milligrams.

20. The method of claim 17, wherein the dose of menthol and/or WS-12 is about 0.0005 milligrams.

21. The method of claim 17, wherein the dose of WS 12 ranges from 0.007 micrograms/kilogram to 0.01 milligrams/kilogram of body weight.

22. The method of claim 17, wherein the dose of WS-12 is about 0.007 micrograms/kilogram of body weight.

23. The method of claim 17, wherein the composition is administered a variable number of times a day.

24. The method of claim 17, wherein the composition is administered from 1 to 4 times a day.

* * * * *